(12) United States Patent
Yeh et al.

(10) Patent No.: US 8,232,381 B2
(45) Date of Patent: Jul. 31, 2012

(54) ISOLATED NUCLEIC ACID MOLECULES FROM TRANSGENIC PAPAYA LINE 18-2-4 RESISTANT TO PAPAYA RINGSPOT VIRUS AND USE THEREOF

(76) Inventors: Shyi-Dong Yeh, Taichung (TW); Huey-Jiunn Bau, Taichung (TW); Ying-Huey Cheng, Taichung (TW); Chung-Chen Fan, Taichung (TW); Yi-Jung Kung, Taichung (TW); Shu Chen, Taichung (TW); Tien-Tsai Su, Taichung (TW)

( * ) Notice: Subject to any disclaimer, the term of this patent is extended or adjusted under 35 U.S.C. 154(b) by 268 days.

(21) Appl. No.: 12/645,607

(22) Filed: Dec. 23, 2009

(65) Prior Publication Data

US 2011/0098459 A1    Apr. 28, 2011

(30) Foreign Application Priority Data

Oct. 28, 2009    (TW) .............................. 098136442 A

(51) Int. Cl.
C07H 21/04 (2006.01)
C12N 15/11 (2006.01)
(52) U.S. Cl. ................................... 536/24.3; 536/24.33
(58) Field of Classification Search .................... 800/280
See application file for complete search history.

(56) References Cited

U.S. PATENT DOCUMENTS

2006/0286576 A1*  12/2006  Lofton-Day et al. ............. 435/6
2008/0263730 A1*  10/2008  Andersen et al. ............. 800/312

OTHER PUBLICATIONS

Diffenbach et al. General tips for PCR primer design (1993) Genome Res. 3: S30-S37.*
Bau et al. Broad-spectrum resistance to differenet geographic stains of Papaya rinspot virus in coat protein gene transgenic papaya (2003) Phytopathology. 93: 112-120.*
Leoni et al. A genome walking strategy for the identification of eukaryotic nucleotide sequences adjacent to known regions (2008) Biotechniques. 44: 229-235.*

* cited by examiner

Primary Examiner — David T Fox
Assistant Examiner — Steven Bernacki
(74) Attorney, Agent, or Firm — Frenkel & Associates, PC

(57) ABSTRACT

Provided is an isolated nucleic acid molecule having a right border flanking region, a left border flanking region and a transgene sequence between the right border flanking region and the left border flanking region, wherein the right border flanking region having at least 90% homology with the sequence set forth in SEQ ID NO: 30; the left border flanking region having at least 90% homology with the sequence set forth in SEQ ID NO: 32; and the transgene sequence having a *papaya* ringspot virus coat protein gene and a promoter operably linked to the *papaya* ringspot virus coat protein gene. Primers, probes and kit derived from the isolated nucleic acid molecule are proved to be useful for identifying the transgenic *papaya* line 18-2-4 in a specific, reproducible, sensitive and reliable way.

1 Claim, 8 Drawing Sheets

16-0-1 RB sequences

18-2-4 RB sequences

Delta Rn vs Cycle 18-2-4 papain → ← PRSV CP

Cycle

FIG. 7c

Delta Rn vs Cycle 18-2-4 homo.

papain → ← PRSV CP

Cycle

FIG. 7d

SEQUENCE LISTING

<160> NUMBER OF SEQ ID NOS: 35

<210> SEQ ID NO 1
<211> LENGTH: 21
<212> TYPE: DNA
<213> ORGANISM: Artificial
<220> FEATURE:
<223> OTHER INFORMATION: 35S-F, primer target to 35S promoter

<400> SEQUENCE: 1
cagctatgac catgattacg c                                           21

-continued

```
<210> SEQ ID NO 2
<211> LENGTH: 18
<212> TYPE: DNA
<213> ORGANISM: Artificial
<220> FEATURE:
<223> OTHER INFORMATION: 35S-R, primer target to 35S promoter

<400> SEQUENCE: 2
tcttgcgaag gatagtgg                                                    18

<210> SEQ ID NO 3
<211> LENGTH: 18
<212> TYPE: DNA
<213> ORGANISM: Artificial
<220> FEATURE:
<223> OTHER INFORMATION: nos-1, primer target to nos terminator

<400> SEQUENCE: 3
tgccggtctt gcgatgat                                                    18

<210> SEQ ID NO 4
<211> LENGTH: 22
<212> TYPE: DNA
<213> ORGANISM: Artificial
<220> FEATURE:
<223> OTHER INFORMATION: nos-2, primer target to nos terminator

<400> SEQUENCE: 4
atgtataatt gcgggactct aa                                               22

<210> SEQ ID NO 5
<211> LENGTH: 20
<212> TYPE: DNA
<213> ORGANISM: Artificial
<220> FEATURE:
<223> OTHER INFORMATION: npt-1 primer target to nptII

<400> SEQUENCE: 5
ataatctgca ccggatctgg                                                  20

<210> SEQ ID NO 6
<211> LENGTH: 20
<212> TYPE: DNA
<213> ORGANISM: Artificial
<220> FEATURE:
<223> OTHER INFORMATION: npt-2 primer target to nptII

<400> SEQUENCE: 6
ccgctcagaa gaactcgtca                                                  20

<210> SEQ ID NO 7
<211> LENGTH: 20
<212> TYPE: DNA
<213> ORGANISM: Artificial
<220> FEATURE:
<223> OTHER INFORMATION: PRSV-F, primer target to transgene

<400> SEQUENCE: 7
tccaagaatg aagctgtgga                                                  20

<210> SEQ ID NO 8
<211> LENGTH: 20
<212> TYPE: DNA
<213> ORGANISM: Artificial
<220> FEATURE:
<223> OTHER INFORMATION: PRSV-R, primer target to transgene

<400> SEQUENCE: 8
```

-continued gtgcatgtct ctgttgacat    20

<210> SEQ ID NO 9
<211> LENGTH: 22
<212> TYPE: DNA
<213> ORGANISM: Artificial
<220> FEATURE:
<223> OTHER INFORMATION: Ap1, primer target to adaptor

<400> SEQUENCE: 9
gtaatacgac tcactatagg gc    22

<210> SEQ ID NO 10
<211> LENGTH: 19
<212> TYPE: DNA
<213> ORGANISM: Artificial
<220> FEATURE:
<223> OTHER INFORMATION: Ap2, primer target to adaptor

<400> SEQUENCE: 10
actatagggc acgcgtggt    19

<210> SEQ ID NO 11
<211> LENGTH: 23
<212> TYPE: DNA
<213> ORGANISM: Artificial
<220> FEATURE:
<223> OTHER INFORMATION: S18, primer target to nos promoter

<400> SEQUENCE: 11
acgcgcaata atggtttctg acg    23

<210> SEQ ID NO 12
<211> LENGTH: 22
<212> TYPE: DNA
<213> ORGANISM: Artificial
<220> FEATURE:
<223> OTHER INFORMATION: Papa27, primer target to nos promoter

<400> SEQUENCE: 12
gcgtcatcgg cggggtcat aa    22

<210> SEQ ID NO 13
<211> LENGTH: 20
<212> TYPE: DNA
<213> ORGANISM: Artificial
<220> FEATURE:
<223> OTHER INFORMATION: P1, primer target to transgene

<400> SEQUENCE: 13
caaacactcg cgccactcaa    20

<210> SEQ ID NO 14
<211> LENGTH: 24
<212> TYPE: DNA
<213> ORGANISM: Artificial
<220> FEATURE:
<223> OTHER INFORMATION: Papa52, primer target to nos terminator

<400> SEQUENCE: 14
tgttgccggt cttgcgatga ttat    24

<210> SEQ ID NO 15
<211> LENGTH: 21
<212> TYPE: DNA
<213> ORGANISM: Artificial

```
<220> FEATURE:
<223> OTHER INFORMATION: Papa34, primer target to nos terminator

<400> SEQUENCE: 15
caacgtcgtg actgggaaaa c                                              21

<210> SEQ ID NO 16
<211> LENGTH: 20
<212> TYPE: DNA
<213> ORGANISM: Artificial
<220> FEATURE:
<223> OTHER INFORMATION: N1, primer target to nos terminator

<400> SEQUENCE: 16
gcccgctcct ttcgctttct                                                20

<210> SEQ ID NO 17
<211> LENGTH: 21
<212> TYPE: DNA
<213> ORGANISM: Artificial
<220> FEATURE:
<223> OTHER INFORMATION: Papa31, primer target to RB flanking sequences
      of 16-0-1

<400> SEQUENCE: 17
ttgttctaat aaggttgcta c                                              21

<210> SEQ ID NO 18
<211> LENGTH: 23
<212> TYPE: DNA
<213> ORGANISM: Artificial
<220> FEATURE:
<223> OTHER INFORMATION: Papa32, primer target to RB flanking sequences
      of 18-2-4

<400> SEQUENCE: 18
aatatcaaat ggacgtgtta gtg                                            23

<210> SEQ ID NO 19
<211> LENGTH: 24
<212> TYPE: DNA
<213> ORGANISM: Artificial
<220> FEATURE:
<223> OTHER INFORMATION: Papa56, primer target to a context upstream of
      LB of T-DNA

<400> SEQUENCE: 19
gttattaagt tgtctaagcg tcaa                                           24

<210> SEQ ID NO 20
<211> LENGTH: 27
<212> TYPE: DNA
<213> ORGANISM: Artificial
<220> FEATURE:
<223> OTHER INFORMATION: Papa57, primer target to LB flanking sequences
      of 16-0-1

<400> SEQUENCE: 20
agacatatat catcaagacc atagtag                                        27

<210> SEQ ID NO 21
<211> LENGTH: 19
<212> TYPE: DNA
<213> ORGANISM: Artificial
<220> FEATURE:
<223> OTHER INFORMATION: Papa58, primer target to a context upstream of
      LB of T-DNA
```

```
<400> SEQUENCE: 21
gtcttgcgat gattatcat                                              19

<210> SEQ ID NO 22
<211> LENGTH: 26
<212> TYPE: DNA
<213> ORGANISM: Artificial
<220> FEATURE:
<223> OTHER INFORMATION: Papa59, primer target to LB flanking sequences
      of 18-2-4

<400> SEQUENCE: 22
tggttatcaa tatagcaatt atgtag                                      26

<210> SEQ ID NO 23
<211> LENGTH: 20
<212> TYPE: DNA
<213> ORGANISM: Artificial
<220> FEATURE:
<223> OTHER INFORMATION: S9-2, primer target to PRSV CP gene for qPCR

<400> SEQUENCE: 23
agtaacgcgg cagaggcata                                             20

<210> SEQ ID NO 24
<211> LENGTH: 22
<212> TYPE: DNA
<213> ORGANISM: Artificial
<220> FEATURE:
<223> OTHER INFORMATION: S10-2, primer target to PRSV CP gene for qPCR

<400> SEQUENCE: 24
gagccctatc aggtgttttc ga                                          22

<210> SEQ ID NO 25
<211> LENGTH: 23
<212> TYPE: DNA
<213> ORGANISM: Artificial
<220> FEATURE:
<223> OTHER INFORMATION: S5, primer target to papain gene for qPCR

<400> SEQUENCE: 25
tgggtttgtc atttggtgat ttt                                         23

<210> SEQ ID NO 26
<211> LENGTH: 26
<212> TYPE: DNA
<213> ORGANISM: Artificial
<220> FEATURE:
<223> OTHER INFORMATION: S6, primer target to papain gene for qPCR

<400> SEQUENCE: 26
gtctttcagt ggatgtcaag tcattt                                      26

<210> SEQ ID NO 27
<211> LENGTH: 21
<212> TYPE: DNA
<213> ORGANISM: Artificial
<220> FEATURE:
<223> OTHER INFORMATION: Fam, PRSV probe

<400> SEQUENCE: 27
ttagtctcgc tagatatgct t                                           21

<210> SEQ ID NO 28
<211> LENGTH: 18
```

```
<212> TYPE: DNA
<213> ORGANISM: Artificial
<220> FEATURE:
<223> OTHER INFORMATION: Vic, papain probe

<400> SEQUENCE: 28
ctattgtggg ttattctc                                                   18

<210> SEQ ID NO 29
<211> LENGTH: 337
<212> TYPE: DNA
<213> ORGANISM: Carica papaya L.
<220> FEATURE:
<223> OTHER INFORMATION: RB flanking sequences of 16-0-1

<400> SEQUENCE: 29 tattttaac ataatttaat aactgtaatc ttattatata ctagtaattt aaattctcaa      60
ctccattaaa ttcaacatta ttcaaactta aataaaatat aaaattttaa ctattagatt    120
ataatgttat taattaccat taaagagatt agtagatatt cttctatttt ttgttatttg    180
attatcaatt gttctaataa ggttgctaca cttagagaac atctggtggt atcaccccag    240
tcttagtttg atagtttatt attctgattt tgtttgttaa aatttctcat tttctttgga    300
tatctgccta ttttgaaatt tggatactat ctcattc                            337

<210> SEQ ID NO 30
<211> LENGTH: 422
<212> TYPE: DNA
<213> ORGANISM: Carica papaya L.
<220> FEATURE:
<223> OTHER INFORMATION: RB flanking sequences of 18-2-4

<400> SEQUENCE: 30
tattgataaa attagagtaa tactaataaa tgctacaaaa ataaaagtga caataatagt     60
aataataatg ataaaaataa taatataatt aacatgacag aataaataat agtaacaata    120
attaataata ataagaataa cagtaagtat aagttacaat aatagagtga gacgatagta    180
gaatggttat aacattaata atatcaaatg gacgtgttag tgatggtagc attacaatgg    240
tattaacgtc attattgttg acaacaataa tatagtaatt atggaagtga tgagatagag    300
gtcataagaa ttgtaaaata ggagacgacg acaaaaatag tagtagtgat gaagaaaata    360
acaaaataac aattatgaga acaaagtgat gataacatca ataacaaatt aataaataat    420
aa                                                                   422

<210> SEQ ID NO 31
<211> LENGTH: 237
<212> TYPE: DNA
<213> ORGANISM: Carica papaya L.
<220> FEATURE:
<223> OTHER INFORMATION: LB flanking sequences of 16-0-1

<400> SEQUENCE: 31
gctctctaaa ttaatttatt ttaatatttt gttttctac tatggtcttg atgatatatg      60
tctttctgca tttaataatt taagtagttt ttaactaaac agtttgggat aaaaacgata    120 tagttttat atatatat atatatat atatataata tgccatagaa ttgctgttaa         180
tataatatca tctattatgt ttaattaatt atgttctaaa attaataata aattta        237

<210> SEQ ID NO 32
<211> LENGTH: 599
<212> TYPE: DNA
<213> ORGANISM: Carica papaya L.
```

```
<220> FEATURE:
<223> OTHER INFORMATION: LB flanking sequences of 18-2-4

<400> SEQUENCE: 32 aatattttt  aaaaaaatta  ttagaatgac  aactacataa  ttgctatatt  gataaccact      60
tatttaaatt  gatgatattt  aatacagtcg  ttaatgatat  tagtatttat  taacatatat     120
aaaaaaaatt  taaatatttt  ttgaaagtaa  aaggataaat  ttgataaaat  gtcaaaataa     180
gagttaatta  aattaaaaat  aattagtata  ggagttaaaa  atggatttt  agtcttttaa      240
aaaataaaaa  aagaaaacaa  atattctttt  accgccaatg  ctaaaataat  taaataaaat     300
ccaagggtat  aagttgcggg  aagaaagcga  cctaggacta  tattttgcgg  aactacagtt     360
ggcacctacc  aattgaacaa  gtaatcgtga  aaaatgatag  aaacagaaca  ggcttgcagc     420
agcctggcga  tgccggcgcc  gactttatcg  ttactggcgg  aggattgcat  atcccttgtg     480
ctttcgctca  catcgcctca  ggacgcatgt  cgggtgtctt  tggtttagtc  ccgagtttcg     540
atccgctgcg  aaatcagacg  tggtctggaa  tcgattttg  ccgtccgaat  acgaggata      599

<210> SEQ ID NO 33
<211> LENGTH: 5449
<212> TYPE: DNA
<213> ORGANISM: Artificial
<220> FEATURE:
<223> OTHER INFORMATION: 16-0-1 T-DNA sequences

<400> SEQUENCE: 33
aacactgata  gtttaaactg  aaggcgggaa  acgacaatct  gatcatgagc  ggagaattaa      60
gggagtcacg  ttatgacccc  cgccgatgac  gcgggacaag  ccgttttacg  tttggaactg     120
acagaaccgc  aacgttgaag  gagccactca  gccgcgggtt  tctggagttt  aatgagctaa     180
gcacatacgt  cagaaaccat  tattgcgcgt  tcaaaagtcg  cctaaggtca  ctatcagcta     240
gcaaatattt  cttgtcaaaa  atgctccact  gacgttccat  aaattcccct  cggtatccaa     300
ttagagtctc  atattcactc  tcaatccaaa  taatctgcac  cggatctgga  tcgtttcgca     360
tgattgaaca  agatggattg  cacgcaggtt  ctccggccgc  ttgggtggag  aggctattcg     420
gctatgactg  ggcacaacag  acaatcggct  gctctgatgc  cgccgtgttc  cggctgtcag     480
cgcaggggcg  cccggttctt  tttgtcaaga  ccgacctgtc  cggtgccctg  aatgaactgc     540
aggacgaggc  agcgcggcta  tcgtggctgg  ccacgacggg  cgttccttgc  gcagctgtgc     600
tcgacgttgt  cactgaagcg  ggaagggact  ggctgctatt  gggcgaagtg  ccggggcagg     660
atctcctgtc  atctcacctt  gctcctgccg  agaaagtatc  catcatggct  gatgcaatgc     720
ggcggctgca  tacgcttgat  ccggctacct  gcccattcga  ccaccaagcg  aaacatcgca     780
tcgagcgagc  acgtactcgg  atggaagccg  gtcttgtcga  tcaggatgat  ctggacgaag     840
agcatcaggg  gctcgcgcca  gccgaactgt  tcgccaggct  caaggcgcgc  atgcccgacg     900
gcgatgatct  cgtcgtgacc  catggcgatg  cctgcttgcc  gaatatcatg  gtggaaaatg     960
gccgcttttc  tggattcatc  gactgtggcc  ggctgggtgt  ggcggaccgc  tatcaggaca    1020
tagcgttggc  tacccgtgat  attgctgaag  agcttggcgg  cgaatgggct  gaccgcttcc    1080
tcgtgcttta  cggtatcgcc  gctcccgatt  cgcagcgcat  cgccttctat  cgccttcttg    1140
acgagttctt  ctgagcggga  ctctggggtt  cgaaatgacc  gaccaagcga  cgcccaacct    1200
gccatcacga  gatttcgatt  ccaccgccgc  cttctatgaa  aggttgggct  tcggaatcgt    1260
tttccgggac  gccggctgga  tgatcctcca  gcgcggggat  ctcatgctgg  agttcttcgc    1320
ccacgggatc  tctgcggaac  aggcggtcga  aggtgccgat  atcattacga  cagcaacggc    1380
```

```
cgacaagcac aacgccacga tcctgagcga caatatgatc gggcccggcg tccacatcaa    1440
cggcgtcggc ggcgactgcc caggcaagac cgagatgcac cgcgatatct tgctgcgttc    1500
ggatattttc gtggagttcc cgccacagac ccggatgatc cccgatcgtt caaacatttg    1560
gcaataaagt ttcttaagat tgaatcctgt tgccggtctt gcgatgatta tcatataatt    1620
tctgttgaat tacgttaagc atgtaataat taacatgtaa tgcatgacgt tatttatgag    1680
atgggttttt atgattagag tcccgcaatt atacatttaa tacgcgatag aaaacaaaat    1740
atagcgcgca aactaggata aattatcgcg cgcggtgtca tctatgttac tagatcgggc    1800
ctcctgtcaa tgctggcggc ggctctggtg gtggttctgg tggcggctct gagggtggtg    1860
gctctgaggg tggcggttct gagggtggcg gctctgaggg aggcggttcc ggtggtggct    1920
ctggttccgg tgattttgat tatgaaaaga tggcaaacgc taataagggg gctatgaccg    1980
aaaatgccga tgaaaacgcg ctacagtctg acgctaaagg caaacttgat tctgtcgcta    2040
ctgattacgg tgctgctatc gatggtttca ttggtgacgt ttccggcctt gctaatggta    2100
atggtgctac tggtgatttt gctggctcta attcccaaat ggctcaagtc ggtgacggtg    2160
ataattcacc tttaatgaat aatttccgtc aatatttacc ttccctccct caatcggttg    2220
aatgtcgccc ttttgtcttt ggcccaatac gcaaaccgcc tctccccgcg cgttggccga    2280
ttcattaatg cagctggcac gacaggtttc ccgactggaa agcgggcagt gagcgcaacg    2340
caattaatgt gagttagctc actcattagg caccccaggc tttacacttt atgcttccgg    2400
ctcgtatgtt gtgtggaatt gtgagcggat aacaatttca cacaggaaac agctatgacc    2460
atgattacgc caagcttgca tgcctgcagg tccccagatt agccttttca atttcagaaa    2520
gaatgctaac ccacagatgg ttagagaggc ttacgcagca ggtctcatca agacgatcta    2580
cccgagcaat aatctccagg aaatcaaata ccttcccaag aaggttaaag atgcagtcaa    2640
aagattcagg actaactgca tcaagaacac agagaaagat atatttctca agatcagaag    2700
tactattcca gtatggacga ttcaaggctt gcttcacaaa ccaaggcaag taatagagat    2760
tggagtctct aaaaaggtag ttcccactga atcaaaggcc atggagtcaa agattcaaat    2820
agaggaccta acagaactcg ccgtaaagac tggcgaacag ttcatacaga gtctcttacg    2880
actcaatgac aagaagaaaa tcttcgtcaa catggtggag cacgacacac ttgtctactc    2940
caaaaatatc aaagatacag tctcagaaga ccaaagggca attgagactt ttcaacaaag    3000
ggtaatatcc ggaaacctcc tcggattcca ttgcccagct atctgtcact ttattgtgaa    3060
gatagtggaa aaggaaggtg gctcctacaa atgccatcat tgcgataaag gaaaggccat    3120
cgttgaagat gcctctgccg acagtggtcc caaagatgga cccccaccca cgaggagcat    3180
cgtggaaaaa gaagacgttc caaccacgtc ttcaaagcaa gtggattgat gtgatatctc    3240
cactgacgta aggcatgacg cacaatccca ctatccttcg caagacccct cctctatata    3300
aggaagttca tttcatttgg agagaacacg ggggactcta gaggatcccc gggtggtcag    3360
tcccttccat ggcgtctaaa aatgaagctg tggataccgg tctgaatgag aagctcaaag    3420
aaaaagaaaa gcagaaagaa aaagaaaaag ataaacaaca agataaagac aatgatggag    3480
ctagtgacgg aaacgatgtg tcaactagca caaaaactgg agagagagat agggatgtca    3540
atgccggaac tagtggaacc ttcactgttc cgaggataaa gtcatttact gataagatga    3600
tcttaccaag aattaaggga aaaactgtcc ttaatttaaa tcatcttctt cagtataatc    3660
cgaaacaagt tgcatctcca aacactcgcg ccactcaatc tcaatttgag aagtggtatg    3720
agggagtgag aaatgattat ggccttaatg ataacgaaat gcaagtaatg ttaaatggtt    3780
```

| | |
|---|---|
| tgatggtttg gtgtatcgaa aatggtacat ctccagatat atctggtgtc tgggttatga | 3840 |
| tggatgggga aacccaagtc gattatccca ttaaaccttt gattgaacac gcaactcctt | 3900 |
| catttaggca aatcatggct cacttcagta acgcggcaga ggcatacatc gcgaagagga | 3960 |
| atgcaactga gaagtacatg ccgcggtatg gaatcaagag aaatttgact gacattagtc | 4020 |
| tcgctagata tgcttttcgat ttctatgagg tgaattcgaa aacacctgat agggctcgtg | 4080 |
| aagctcatat gcagatgaag gctgcagcgc tacgcaatac taatcgcaaa atgtttggaa | 4140 |
| tggacggcag tgtcagtaac aaggaagaaa acacggagag acacacagtg gaagatgtca | 4200 |
| acagagacat gcactctctc ctgggtatgc gcaattgaat actcgcgcta gtgtgtttgt | 4260 |
| cgggcctggc tcgaccctgt ttcaccttat aatactatgt aagcattaga atatagtgtg | 4320 |
| gctgcgccac cgcttctatt ttacagtgag ggtagccctc cgtgctttta gtgttattcg | 4380 |
| agttctctga gtctccatac agtgtgggtg gcccacgtgc tattcgagcc tcttggaatg | 4440 |
| agagaaaaaa aaaaaaaaaa aaaaaaaaaa aactcgagga attcggtacc cgggttcga | 4500 |
| aatcgataag cttggatccg gagagctcga atttccccga tcgttcaaac atttggcaat | 4560 |
| aaagtttctt aagattgaat cctgttgccg gtcttgcgat gattatcata taatttctgt | 4620 |
| tgaattacgt taagcatgta ataattaaca tgtaatgcat gacgttattt atgagatggg | 4680 |
| tttttatgat tagagtcccg caattataca tttaatacgc gatagaaaac aaaatatagc | 4740 |
| gcgcaaacta ggataaatta tcgcgcgcgg tgtcatctat gttactagat cgggaattca | 4800 |
| ctggccgtcg ttttacaacg tcgtgactgg gaaaaccctg gcgttaccca acttaatcgc | 4860 |
| cttgcagcac atccccctt cgccagctgg cgtaatagcg aagaggcccg caccgatcgc | 4920 |
| ccttcccaac agttgcgcag cctgaatggc gcccgctcct ttcgctttct tcccttcctt | 4980 |
| tctcgccacg ttcgccggct ttccccgtca agctctaaat cggggctcc ctttagggtt | 5040 |
| ccgatttagt gctttacggc acctcgaccc caaaaaactt gatttgggtg atggttcacg | 5100 |
| tagtgggcca tcgccctgat agacggtttt tcgccctttg acgttggagt ccacgttctt | 5160 |
| taatagtgga ctcttgttcc aaactggaac aacactcaac cctatctcgg gctattcttt | 5220 |
| tgatttataa gggattttgc cgatttcgga accaccatca aacaggattt tgcctgctg | 5280 |
| gggcaaacca gcgtggaccg cttgctgcaa ctctctcagg gccaggcggt gaagggcaat | 5340 |
| cagctgttgc ccgtctcact ggtgaaaaga aaaaccaccc cagtacatta aaaacgtccg | 5400 |
| caatgtgtta ttaagttgtc taagcgtcaa tttgtttaca ccacaatat | 5449 |

<210> SEQ ID NO 34
<211> LENGTH: 4666
<212> TYPE: DNA
<213> ORGANISM: Artificial
<220> FEATURE:
<223> OTHER INFORMATION: 18-2-4 T-DNA sequences

<400> SEQUENCE: 34

| | |
|---|---|
| gatagtttaa actgaaggcg ggaaacgaca atctgatcat gagcggagaa ttaagggagt | 60 |
| cacgttatga cccccgccga tgacgcggga caagccgttt tacgtttgga actgacagaa | 120 |
| ccgcaacgtt gaaggagcca ctcagccgcg ggtttctgga gtttaatgag ctaagcacat | 180 |
| acgtcagaaa ccattattgc gcgttcaaaa gtcgcctaag gtcactatca gctagcaaat | 240 |
| atttcttgtc aaaaatgctc cactgacgtt ccataaattc ccctcggtat ccaattagag | 300 |
| tctcatattc actctcaatc caaataatct gcaccggatc tggatcgttt cgcatgattg | 360 |
| aacaagatgg attgcacgca ggttctccgg ccgcttgggt ggagaggcta ttcggctatg | 420 |

```
actgggcaca acagacaatc ggctgctctg atgccgccgt gttccggctg tcagcgcagg      480
ggcgcccggt tcttttgtc aagaccgacc tgtccggtgc cctgaatgaa ctgcaggacg       540
aggcagcgcg gctatcgtgg ctggccacga cgggcgttcc ttgcgcagct gtgctcgacg      600
ttgtcactga agcgggaagg gactggctgc tattgggcga agtgccgggg caggatctcc      660
tgtcatctca ccttgctcct gccgagaaag tatccatcat ggctgatgca atgcggcggc      720
tgcatacgct tgatccggct acctgcccat tcgaccacca agcgaaacat cgcatcgagc      780
gagcacgtac tcggatggaa gccggtcttg tcgatcagga tgatctggac gaagagcatc      840
aggggctcgc gccagccgaa ctgttcgcca ggctcaaggc gcgcatgccc gacggcgatg      900
atctcgtcgt gacccatggc gatgcctgct tgccgaatat catggtggaa aatggccgct      960
tttctggatt catcgactgt ggccggctgg gtgtggcgga ccgctatcag gacatagcgt     1020
tggctacccg tgatattgct gaagagcttg gcggcgaatg ggctgaccgc ttcctcgtgc     1080
tttacggtat cgccgctccc gattcgcagc gcatcgcctt ctatcgcctt cttgacgagt     1140
tcttctgagc gggactctgg ggttcgaaat gaccgaccaa gcgacgccca acctgccatc     1200
acgagatttc gattccaccg ccgccttcta tgaaaggttg gcttcggaa tcgttttccg      1260 ggacgccggc tggatgatcc tccagcgcgg ggatctcatg ctggagttct cgcccacgg     1320 gatctctgcg gaacaggcgg tcgaaggtgc cgatatcatt acgacagcaa cggccgacaa     1380
gcacaacgcc acgatcctga cgacaatat gatcgggccc ggcgtccaca tcaacggcgt     1440
cggcggcgac tgcccaggca agaccgagat gcaccgcgat atcttgctgc gttcggatat     1500
tttcgtggag ttcccgccac agacccggat gatccccgat cgttcaaaca tttggcaata     1560
aagtttctta agattgaatc ctgttgccgg tcttgcgatg attatcatat aatttctgtt     1620
gaattacgtt aagcatgtaa taattaacat gtaatgcatg acgttattta tgagatgggt     1680
ttttatgatt agagtcccgc aattatacat ttaatacgcg atagaaaaca aaatatagcg     1740
cgcaaactag gataaattat cgcgcgcggt gtcatctatg ttactagatc gggcctcctg     1800
tcaatgctgg cggcggctct ggtggtggtt ctggtggcgg ctctgagggt ggtggctctg     1860
agggtggcgg ttctgagggt ggcggctctg agggaggcgg ttccggtggt ggctctggtt     1920
ccggtgattt tgattatgaa aagatggcaa acgctaataa gggggctatg accgaaaatg     1980
ccgatgaaaa cgcgctacag tctgacgcta aaggcaaact tgattctgtc gctactgatt     2040
acggtgctgc tatcgatggt ttcattggtg acgtttccgg ccttgctaat ggtaatggtg     2100
ctactggtga ttttgctggc tctaattccc aaatggctca agtcggtgac ggtgataatt     2160
cacctttaat gaataatttc cgtcaatatt taccttccct ccctcaatcg gttgaatgtc     2220
gcccttttgt ctttggccca atacgcaaac cgcctctccc cgcgcgttgg ccgattcatt     2280
aatgcagctg gcacgacagg tttcccgact ggaaagcggg cagtgagcgc aacgcaatta     2340
atgtgagtta gctcactcat taggcacccc aggctttaca ctttatgctt ccggctcgta     2400
tgttgtgtgg aattgtgagc ggataacaat ttcacacagg aaacagctat gaccatgatt     2460
acgccaagct tgcatgcctg caggtcccca gattagcctt ttcaatttca gaaagaatgc     2520
taacccacag atggttagag aggcttacgc agcaggtctc atcaagacga tctacccgag     2580
caataatctc caggaaatca aataccttcc caagaaggtt aaagatgcag tcaaaagatt     2640
caggactaac tgcatcaaga acacagagaa agatatattt ctcaagatca gaagtactat     2700
tccagtatgg acgattcaag gcttgcttca caaaccaagg caagtaatag agattggagt     2760
ctctaaaaag gtagttccca ctgaatcaaa ggccatggag tcaaagattc aaatagagga     2820
```

```
cctaacagaa ctcgccgtaa agactggcga acagttcata cagagtctct tacgactcaa    2880
tgacaagaag aaaatcttcg tcaacatggt ggagcacgac acacttgtct actccaaaaa    2940
tatcaaagat acagtctcag aagaccaaag ggcaattgag acttttcaac aaagggtaat    3000
atccggaaac ctcctcggat tccattgccc agctatctgt cactttattg tgaagatagt    3060
ggaaaaggaa ggtggctcct acaaatgcca tcattgcgat aaaggaaagg ccatcgttga    3120
agatgcctct gccgacagtg gtcccaaaga tggaccccca cccacgagga gcatcgtgga    3180 aaagaagac gttccaacca cgtcttcaaa gcaagtggat tgatgtgata tctccactga    3240
cgtaagggat gacgcacaat cccactatcc ttcgcaagac ccttcctcta tataaggaag    3300
ttcatttcat ttggagagaa cacggggac tctagaggat ccccgggtgg tcagtccctt      3360
ccatggcgtc taaaaatgaa gctgtggata ccggtctgaa tgagaagctc aaagaaaaag    3420
aaaagcagaa agaaaagaa aaagataaac aacaagataa agacaatgat ggagctagtg     3480
acggaaacga tgtgtcaact agcacaaaaa ctggagagag agatagggat gtcaatgccg    3540
gaactagtgg aaccttcact gttccgagga taaagtcatt tactgataag atgatcttac    3600
caagaattaa gggaaaaact gtccttaatt taaatcatct tcttcagtat aatccgaaac    3660
aagttgacat ctcaaacact cgcgccactc aatctcaatt tgagaagtgg tatgagggag    3720
tgagaaatga ttatggcctt aatgataacg aaatgcaagt aatgttaaat ggtttgatgg    3780
tttggtgtat cgaaaatggt acatctccag atatatctgg tgtctgggtt atgatggatg    3840
gggaaaccca agtcgattat cccattaaac ctttgattga acacgcaact ccttcattta    3900
ggcaaatcat ggctcacttc agtaacgcgg cagaggcata catcgcgaag aggaatgcaa    3960
ctgagaagta catgccgcgg tatggaatca agagaaattt gactgacatt agtctcgcta    4020
gatatgcttt cgatttctat gaggtgaatt cgaaaacacc tgatagggct cgtgaagctc    4080
atatgcagat gaaggctgca gcgctacgca atactaatcg caaaatgttt ggaatggacg    4140
gcagtgtcag taacaaggaa gaaaacacgg agagacacac agtggaagat gtcaacagag    4200
acatgcactc tctcctgggt atgcgcaatt gaatactcgc gctagtgtgt ttgtcgggcc    4260
tggctcgacc ctgtttcacc ttataatact atgtaagcat tagaatatag tgtggctgcg    4320
ccaccgcttc tattttacag tgagggtagc cctccgtgct tttagtgtta ttcgagttct    4380
ctgagtctcc atacagtgtg ggtggcccac gtgctattcg agcctcttgg aatgagagaa    4440 aaaaaaaaa aaaaaaaaa aaaaaactcg aggaattcgg tacccggggt tcgaaatcga    4500
taagcttgga tccggagagc tcgaatttcc ccgatcgttc aaacatttgg caataaagtt    4560
tcttaagatt gaatcctgtt gccggtcttg cgatgattat catataattt ctgttgaatt    4620
acgttaagca tgtaataatt aacatgtaat gcatgacgtt atttat               4666

<210> SEQ ID NO 35
<211> LENGTH: 48
<212> TYPE: DNA
<213> ORGANISM: Artificial
<220> FEATURE:
<223> OTHER INFORMATION: Adaptor

<400> SEQUENCE: 35
gtaatacgac tcactatagg gcacgcgtgg tcgacggccc gggcaggt                 48
```

ISOLATED NUCLEIC ACID MOLECULES FROM TRANSGENIC PAPAYA LINE 18-2-4 RESISTANT TO PAPAYA RINGSPOT VIRUS AND USE THEREOF

BACKGROUND OF THE INVENTION

1. Field of the Invention

The present invention correlates to a nucleic acid molecule containing sequence flanking T-DNA insert in transgenic papaya line 18-2-4, which are useful for specifically, reproducibility, sensitively and reliably identifying or reproducing transgenic papaya line resistant to papaya ringspot virus.

2. Description of the Prior Arts

Papaya (Carica papaya L.) is widely grown in tropical and subtropical areas. A destructive disease caused by Papaya ringspot virus (PRSV) is the major obstacle to large-scale commercial production of papaya throughout the world (Purcifull et al., 1984, CMI/AAB Descriptions of Plant Viruses. No. 292). PRSV was first found in southern areas of Taiwan in 1975 (Wang et al., 1978, Plant Prot Bull 20:133-140). Since then it has destroyed most of the papaya production in commercial orchards. PRSV is a member of the genus Potyvirus (Fauquet et al., 2005, Virus Taxonomy: VIIIth Report of the International Committee on Taxonomy of Viruses. ELSEVIER, San Diego), the largest and economically most important plant virus group. The virus is naturally transmitted by aphids in a non-persistent manner and induces symptoms of mosaic and distortion on leaves, streaks on petiole and stem, and stunting in growth, resulting in drastic reduction in fruit quality and yield (Purcifull et al., 1984, supra).

Several control measures have been used to protect papaya plants from PRSV infection, including the selection of planting time to avoid the peak of winged aphids, the use of silver mulch to repel aphids from visiting seedlings, and the application of cross-protection using mild strains of PRSV (Yeh et al., 1988, Plant Dis 72:375-380; Yeh and Gonsalves, 1994, Adv Dis Vector Res. 10:237-257). However, none of these methods provides a long period of effective protection against PRSV. Currently, cultivation under netting to prevent papaya plants from infection by aphid-transmitted PRSV has become an effective control method in Taiwan. However, high cost of the netting, creation of environmental hazard owing to the difficult degradation of plastic material in nature, and high risk of destruction by tropical storms are major concerns (Bau et al., 2003, Phytopathology 93:112-120).

In recent years, based on the concept of pathogen-derived resistance (PDR) (Sanford and Johnson, 1985, J Theor Biol 113:395-405), the development of transgenic plants containing a genomic segment of a plant virus is widely used as a strategy to control corresponding plant viruses (Beachy, 1997, Curr Opin Biotech 8:215-220). In most cases, the mechanism of resistance occurs posttranscriptionally, by a RNA-mediated process that targets both the viral RNA and transgenic mRNA for degradation in a sequence-specific manner (English et al., 1996, Plant Cell 8:179-188; Lindbo et al., 1993, Plant Cell 5:1749-1759; Sijen and Kooter, 2000, Bioessays. 22:520-531; Vaucheret et al., 1998, Plant J 16:651-659). The coat protein (CP) gene of PRSV has been transferred into papaya via particle bombardment (Fitch et al., 1990, Plant Cell Rep 9:189-194) and transgenic lines highly resistant to PRSV infection have been selected (Fitch et al., 1992, Bio/Technology 10:1466-1472; Lius et al., 1997, Mol. Breed. 3:161-168).

Transgenic papaya lines have been successfully commercialized in Hawaii since 1998 (Gonsalves, 2002, Curr Top Microbiol Immunol 266:73-83; Tripathi et al., 2007, Methods Mol Biol 354:197-240). In Taiwan, transgenic papaya lines carrying the CP gene of a Taiwan severe strain PRSV YK, have also been generated by Agrobacterium-mediated transformation (Cheng et al., 1996, Plant Cell Rep 16:127-132). When the transgenic papaya lines are challenged with PRSV YK, their reactions to virus infection range from high susceptibility to complete resistance (Bau et al., 2003, Phytopathology 93:112-120). The transgenic lines 16-0-1, 17-0-1, 17-0-5 and 18-2-4 provide broad-spectrum resistance against PRSV strains from different geographic origins under greenhouse conditions (Bau et. al., 2003, supra) and high degrees of resistance during field tests (Bau et al., 2004, Plant Dis 88:594-599). These lines have great potential for control of PRSV in different geographic areas.

It was observed that the highly resistant lines 16-0-1, 17-0-5 and 18-2-4 display a strong strain-specific resistance at young development stage (5-cm height), but not other lines, such as 18-0-9 and 19-0-1. Accordingly, the insertion locus of T-DNA in papaya genome must have its unique characteristics, particular to the papaya line 18-2-4. Once the locus of the genome inserted by the T-DNA is elucidated, it will be helpful for generating a stable papaya line with broad spectrum of resistance against PRSV strains since people can utilize the character of the sequence of T-DNA insert in combination with genome sequences flanking the T-DNA to modify various papaya strains to obtain resistances to PRSV by homologous recombination without tedious selections and field tests.

On the other hand, concerns have recently been raised on safety issues of genetically modified organisms (GMOs) (Singh et al., 2006, Appl Microbiol Biotechnol 71: 598-607). Variegated legislations have been applied in different countries for the GM food approval and labeling. According to European Union (EU) regulation (EC) No. 1830/2003, it is required to be able to trace GMO and products derived from GMOs at every stage on market from production to distribution (European Parliament and Council of European Union, 2003, p. 1-5). Also, regulations in Taiwan for GM crop field tests and consequent variety rights also requires the information of genomic sequences flanking the transgene for a particular transgenic line. Therefore, characterization of a particular GMO to provide specific and reliable methods for even-specific detection is crucial to assure regulatory compliance and also important to monitor unauthorized GMO occurrence in markets and plantations.

Accordingly, there is an urgent need for means for generating or identifying transgenic papaya lines with broad-spectrum of resistance against various PRSV strains, as transgenic papaya line 18-2-4, which is specific, reproducible, sensitive and reliable. To overcome the shortcomings, the present invention tends to provide isolated nucleic acids, methods, primers, probes and kit for generating or identifying transgenic papaya line 18-2-4 to mitigate or obviate the aforementioned problems.

SUMMARY OF THE INVENTION

The main objective of the invention is to provide means for identifying or generating transgenic papaya line resistant to papaya ringspot virus.

In a first aspect, the present invention provides an isolated nucleic acid molecule, comprising: a right border flanking region, a left border flanking region and a transgene sequence between the right border flanking region and the left border flanking region, wherein the right border flanking region has at least 90% homology with the sequence set forth in SEQ ID NO: 30; the left border flanking region having at least 90% homology with the sequence set forth in SEQ ID NO: 32; and the transgene sequence having a *papaya* ringspot virus coat protein gene and a promoter operably linked to the *papaya* ringspot virus coat protein gene.

In a second aspect, the present invention provides a primer for amplifying transgenic *papaya* nucleic acid sequence, which is selected from the group consisting of:

a nucleic acid fragment having at least 10 consecutive nucleic acids of the sequence set forth in SEQ ID NO:30 or complementary sequence thereof; and a nucleic acid fragment having at least 10 consecutive nucleic acids of the sequence set forth in SEQ ID NO:32 or complementary sequence thereof.

Preferably, the primer is selected from the group consisting of: Papa32 primer having sequence set forth in SEQ ID NO: 18; and Papa59 primer having sequence set forth in SEQ ID NO: 22.

In a third aspect, the present invention provides a method for identifying transgenic *papaya* line 18-2-4, comprising:

providing a polymerase chain reaction mixture containing a *papaya* nucleic acid sample and a primer pair;

reacting the polymerase chain reaction mixture to form an amplification product;

detecting existence of a predetermined amplified fragment in the amplification product; and determining whether the *papaya* nucleic acid sample contains genomic DNA obtained from transgenic *papaya* line 18-2-4, wherein if existence of the predetermined amplified fragment is detected, then the *papaya* nucleic acid sample contains genomic DNA obtained from transgenic *papaya* line 18-2-4;

wherein the primer pair has a forward primer selected from the group consisting of: a nucleic acid fragment having at least 10 consecutive nucleic acids of the sequence set forth in SEQ ID NO:30; a nucleic acid fragment having at least 10 consecutive nucleic acids of the sequence between positions 3666 and 4666 set forth in SEQ ID NO: 34; a reverse primer selected from the group consisting of: a nucleic acid fragment having a complementary sequence to at least 10 consecutive nucleic acids of the sequence set forth in SEQ ID NO: 32; and a nucleic acid fragment having a complementary sequence to at least 10 consecutive nucleic acids of the sequence between position +1 and +1000 set forth in SEQ ID NO: 34.

Other objectives, advantages and novel features of the invention will become more apparent from the following detailed description when taken in conjunction with the accompanying drawings.

BRIEF DESCRIPTION OF THE DRAWINGS

FIGS. 1*a* to 1*c* illustrate schematic presentation of the regions flanking the inserted T-DNA of transgenic *papaya* lines, wherein FIG. 1*a* illustrates the T-DNA insert in the *papaya* genome, wherein the full region of the T-DNA insert is close-boxed; genomic sequences are open-boxed; RB: right border; LB: left border; P35S: CaMV 35S promoter; Pnos and Tnos: nopaline synthase promoter and terminator, respectively; npt II: neomycin phosphotransferase II; and PRSV CP: the coat protein coding region of *Papaya* ringspot virus;

FIG. 1*b* illustrates the strategy to amplify the genomic sequence flanking the right border, wherein adaptor is black-boxed and adaptor primers (Ap1 and Ap2) and position of right border-specific primers (S18 and Papa27) are indicated;

FIG. 1*c* illustrates the strategy to amplify the genomic sequence flanking the left border, wherein adaptor is black-boxed and adaptor primers (Ap1 and Ap2), positions of left border-specific primers for 16-0-1 and 17-0-5 (Papa34 and N1) and left border-specific primers for 18-2-4 (P1 and Papa52) are indicated;

FIG. 3*a* illustrates the genomic flanking sequence of T-DNA right border from both the transgenic lines 16-0-1 and 17-0-5; and FIG. 3*b* illustrates the genomic sequence flanking T-DNA right border from line 18-2-4;

FIG. 4*a* illustrates the genomic flanking sequence of T-DNA left border from lines 16-0-1 and 17-0-5; and FIG. 4*b* illustrates the genomic flanking sequence of T-DNA left border from line 18-2-4;

Figure 6:
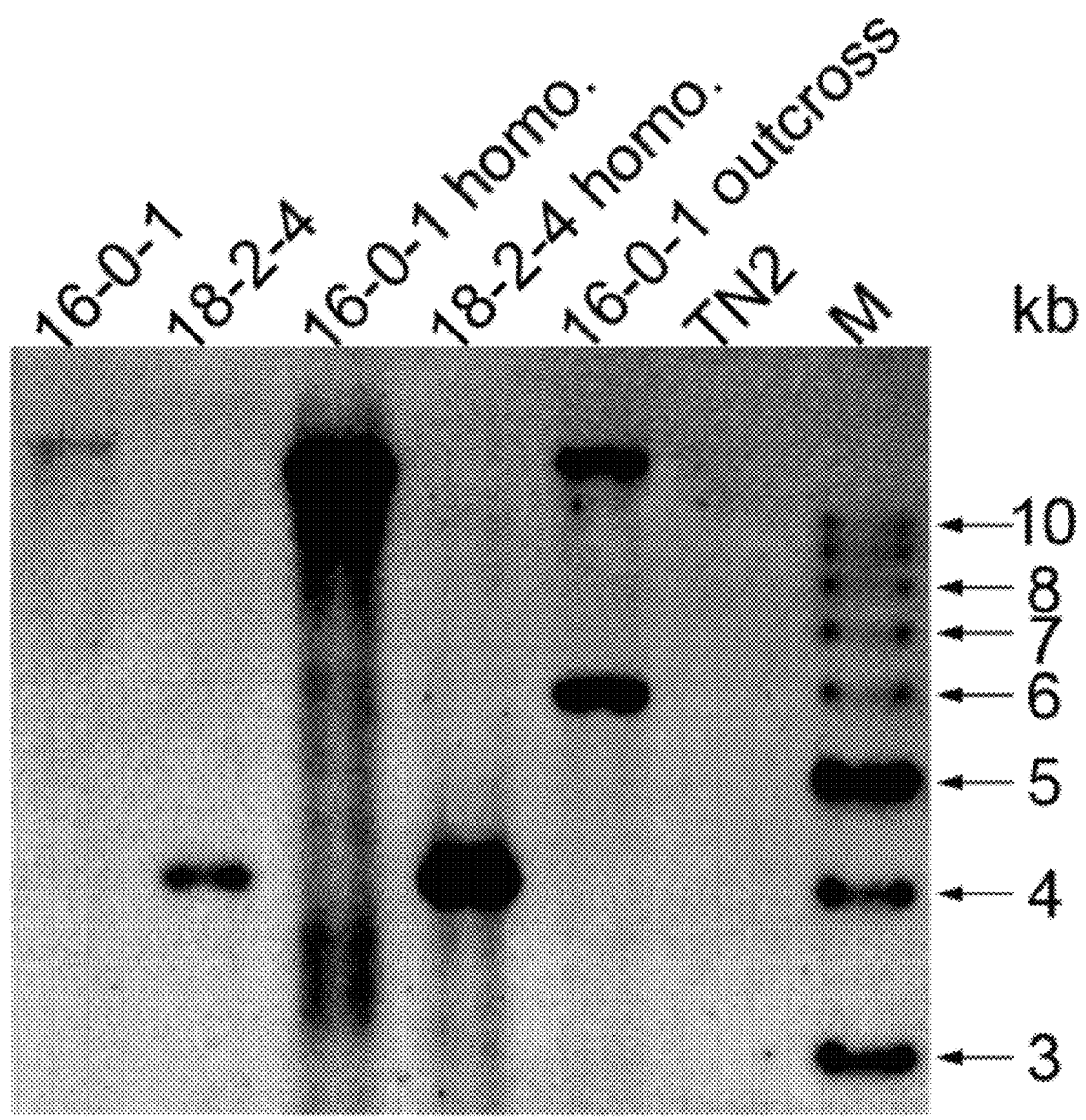
Figure 7A:
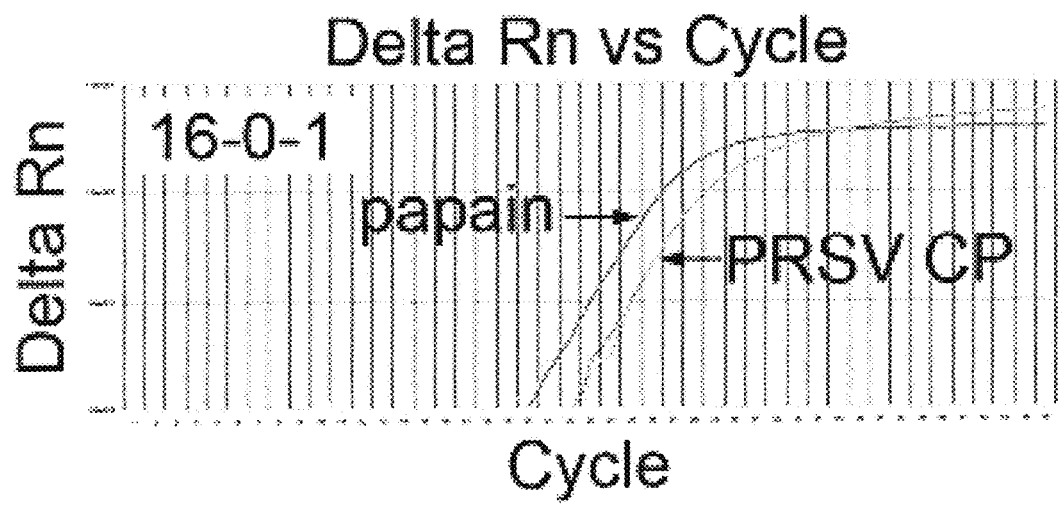
Figure 7B:
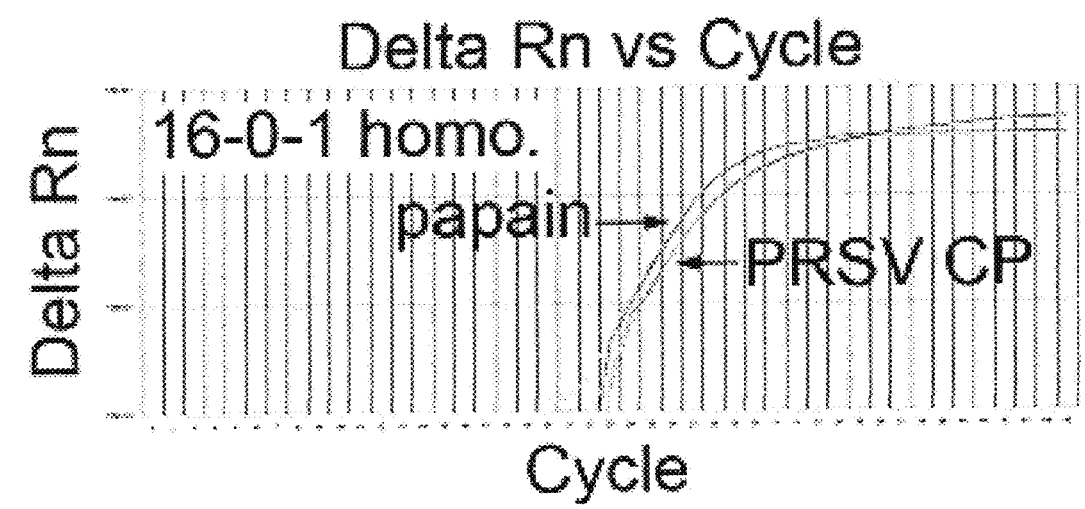

panel (a) illustrates that the primer pair Papa31/Papa27 specific to line 16-0-1 (right border, RB) generated a specific product of 241 bp; panel (b) illustrates that the primer pair Papa32/Papa27 specific to line 18-2-4 (right border, RB) generated a specific product of 384 bp;

panel (c) illustrates that the primer pair Papa56/Papa57 specific to line 16-0-1 (LB) generated specific product of 106 bp; panel (d) illustrates that the primer pair Papa58/Papa59 specific to line 18-2-4 (LB) generated a specific product of 140 bp;

panel (e) illustrates that the primer pair Papa31 and Papa57 designed from RB and LB flanking sequences, respectively, generated a specific product of 227 bp; and panel (f) illustrates that the primer pair Papa32 and Papa59 designed from RB and LB flanking sequence, respectively, generated a specific product of 345 bp;

FIG. 6 illustrates results of determination of PRSV CP transgene copy number by Southern blotting, wherein M represents 1 kb DNA Step Ladder; 16-0-1, 18-2-4: represents hemizygous lines of 16-0-1 and 18-2-4 respectively; 16-0-1 homo. and 18-2-4 homo. represent homozygous progenies of 16-0-1 and 18-2-4 respectively; 16-0-1 outcross represents the progeny from a cross of transgenic line 16-0-1 with an unidentified PRSV CP transgenic line; and TN2 represents non-transgenic *papaya*; and FIGS. 7a to 7d illustrate amplification plots of PRSV CP transgene by real time PCR, wherein the delta Rn value represents the normalized reported fluorescence emission as the reporter dye released from the TaqMan probe;

FIG. 7a illustrates a typical amplification curve for 16-0-1 hemizygous $T_0$ plant;

FIG. 7b illustrates a typical amplification curve for 16-0-1 homozygous $T_1$ plant;

FIG. 7c illustrates a typical amplification curve for 18-2-4 hemizygous $T_0$ plant; and FIG. 7d illustrates a typical amplification curve for 18-2-4 homozygous $T_1$ plant.

DETAILED DESCRIPTION OF THE PREFERRED EMBODIMENT

The commercially valuable transgenic *papaya* lines carrying the coat protein (CP) gene of *Papaya* ringspot virus (PRSV) and conferring virus resistance have been developed in Hawaii and Taiwan in the past decade. Generation of a transgenic *papaya* line with broad-spectrum resistance to different PRSV strains requires vast works of screening and field tests to obtain a stable line. Here, the present invention determined locus of the T-DNA containing PRSV CP gene in transgenic *papaya* line 18-2-4 and analyzed the genomic sequence flanking the right border and the left border of the T-DNA.

Accordingly, a nucleic acid molecule was provided for manufacturing stable *papaya* lines resistant to PRSV. The present invention provides an isolated nucleic acid molecule comprising: a right border flanking region, a left border flanking region and a transgene sequence between the right border flanking region and the left border flanking region, wherein the right border flanking region having at least 90% homology with the sequence set forth in SEQ ID NO: 30; the left border flanking region having at least 90% homology with the sequence set forth in SEQ ID NO: 32; and the transgene sequence having a *papaya* ringspot virus coat protein gene and a promoter operably linked to the *papaya* ringspot virus coat protein gene.

On the other hand, prompt and sensitive protocols for transgene-specific and event-specific detection are required for traceability of these lines to fulfill regulatory requirement in EU and some Asian countries.

For assuring regulatory compliance, detection protocols for characterization of PRSV CP-transgenic *papaya* lines were provided. Transgene-specific products were amplified using different specific primer pairs targeting the sequences of the promoter, the terminator, the selection marker, and the transgene; and the region across the promoter and transgene.

Moreover, after cloning and sequencing the DNA fragments amplified by adaptor ligation-PCR (AL-PCR), the junctions between plant genomic DNA and the T-DNA insert were elucidated.

Furthermore, the present invention also provided an event-specific method targeting the flanking sequences and the transgene for identification of a specific transgenic *papaya* line 18-2-4. The PCR patterns using primers designed from the left or the right flanking DNA sequence of the transgene insert in selected transgenic *papaya* lines were specific and reproducible. The present invention also verified that PRSV CP transgene is integrated into transgenic *papaya* genome in different loci. The copy number of inserted T-DNA was further confirmed by real-time PCR. The event-specific molecular markers developed in this investigation are crucial for regulatory requirements in some countries and intellectual protection. Also, the method, primer and kit in accordance with the present invention are helpful for prompt screening of a homozygote-transgenic progeny in the breeding program.

According to the present invention, the term "homology" refers to degree of similarity between two sequences, which is determined by identical and/or conservative ratio between the sequences. Variation of nucleic acids or amino acids do not necessarily deter characteristics consisting thereof, those nucleic acid sequence or its encoding amino acid sequence having certain homology that will not change the character of the nucleic acid sequence or the activity of the protein are encompassed by the present invention. Preferably, the certain homology is at least 90%.

In a preferred embodiment of the isolated nucleic acid molecule in accordance with the present invention, the promoter is Cauliflower Mosaic Virus 35S promoter (CaMV 35S promoter).

In a preferred embodiment of the isolated nucleic acid molecule in accordance with the present invention, the transgene sequence has at least 90% homology with the sequence set forth in SEQ ID NO: 34.

In a preferred embodiment of the present invention, the isolated nucleic acid molecule consists of the right border flanking region, the left border flanking region and the transgene sequence between the right border flanking region and the left border flanking region, wherein the right border flanking region has the sequence set forth in SEQ ID NO: 30; the left border flanking region has the sequence set forth in SEQ ID NO: 32; and the transgene sequence has the sequence set forth in SEQ ID NO: 34.

According to the present invention, the primer for amplifying transgenic *papaya* nucleic acid sequence is selected from the group consisting of: a nucleic acid fragment having at least 10 consecutive nucleic acids of the sequence set forth in SEQ ID NO: 30 or complementary sequence thereof; and a nucleic acid fragment having at least 10 consecutive nucleic acids of the sequence set forth in SEQ ID NO: 32 or complementary sequence thereof.

Preferably, the primer is selected from the group consisting of: a nucleic acid fragment having at least 15 consecutive nucleic acids of the sequence set forth in SEQ ID NO: 30 or complementary sequence thereof; and a nucleic acid fragment having at least 15 consecutive nucleic acids of the sequence set forth in SEQ ID NO: 32 or complementary sequence thereof.

According to the present invention, the primer is selected from the group consisting of: nucleic acid fragment having sequence set forth in SEQ ID NO: 18 (Papa32 primer); and nucleic acid fragment having sequence set forth in SEQ ID NO: 22 (Papa59 primer).

According to the present invention, the primer as known in the art can be prepared by any chemical or biochemical synthetic methods. For example, nucleic acid can be directly synthesized by a DNA synthesizer. To improve the stability of nucleic acid in cell, a base, glycosyl and phosphoryl group thereof can be subject to chemical modification, such as alkylation, acylation or other similar reactions.

The term "probe" refers to materials recognizing particular sequence and producing signal for detection. The probe as used herein includes nucleic acid fragment labeled with radioactive substance, fluorescence dye and substrate-specific enzyme.

The method for identifying transgenic *papaya* line 18-2-4 in accordance with the present invention comprises steps of:

providing a polymerase chain reaction mixture containing a *papaya* nucleic acid sample and a primer pair;

reacting the polymerase chain reaction mixture to form an amplification product;

detecting existence of a predetermined amplified fragment in the amplification product; and determining whether the *papaya* nucleic acid sample contains genomic DNA obtained from transgenic *papaya* line 18-2-4, wherein if existence of the predetermined amplified fragment is detected, the *papaya* nucleic sample contains genomic DNA obtained from transgenic *papaya* line 18-2-4;

wherein the primer pair has a forward primer selected from the group consisting of: a nucleic acid fragment having at least 10 consecutive nucleic acids of the sequence set forth in SEQ ID NO: 30; and a nucleic acid fragment having at least 10 consecutive nucleic acids of the sequence, preferably, at least 15 consecutive nucleic acids of the sequence, between positions 3666 and 4666 set forth in SEQ ID NO: 34; and a reverse primer selected from the group consisting of: a nucleic acid fragment having a complementary sequence to at least 10 consecutive nucleic acids of the sequence, preferably, at least 15 consecutive nucleic acids of the sequence, set forth in SEQ ID NO: 32; and a nucleic acid fragment having a complementary sequence to at least 10 consecutive nucleic acids of the sequence, preferably, at least 15 consecutive nucleic acids of the sequence, between position +1 and +1000 set forth in SEQ ID NO: 34.

In a preferred embodiment of the present invention, the forward primer is selected from a group consisting of: nucleic acid fragment having sequence set forth in SEQ ID NO: 18 (Papa32 primer); nucleic acid fragment having sequence set forth in SEQ ID NO: 13 (P1 primer); nucleic acid fragment having sequence set forth in SEQ ID NO: 15 (Papa34 primer); nucleic acid fragment having sequence set forth in SEQ ID NO: 14 (Papa52 primer); nucleic acid fragment having sequence set forth in SEQ ID NO: 19 (Papa56 primer); nucleic acid fragment having sequence set forth in SEQ ID NO: 21 (Papa58 primer); and nucleic acid fragment having sequence set forth in SEQ ID NO: 16 (N1 primer); and the reverse primer is selected from the group consisting of: nucleic acid fragment having sequence set forth in SEQ ID NO: 11 (S18 primer); nucleic acid fragment having sequence set forth in SEQ ID NO: 12 (Papa27 primer); and nucleic acid fragment having sequence set forth in SEQ ID NO: 22 (Papa59 primer).

According to the present invention, the term "amplified fragment" refers to a particular fragment amplified by polymerase chain reaction by using nucleic acid as template and primers as described above. For example, when a polymerase chain reaction with Papa32 (SEQ ID NO: 18) as forward primer, Papa27 (SEQ ID NO: 12) as reverse primer and genomic DNA of transgenic *papaya* line 18-2-4 as template was carried out in appropriate conditions, a fragment of 384 base pair would be amplified.

According to the present invention, the polymerase chain reaction mixture as known in the art includes primers, template, polymerase, deoxyribonucleotide triphosphate (dNTP) and reaction buffer and is used in polymerase chain reaction to obtain an amplification product.

In a preferred embodiment of the present invention, said polymerase chain reaction mixture further includes a dye, wherein the dye is capable of binding to the amplified fragment and absorbing an adequate fluorescence and emitting a detectable fluorescence signal, such as but not limited to: SYBR® Green.

According to the present invention, the *papaya* nucleic acid sample can be derived from any parts, such as root, stem, leave, flower, fruit and seed, of *papaya* by any method for extracting nucleic acid in the art. Preferably, the *papaya* nucleic acid sample is isolated from the leaves of *papaya* by cetyltrimethylammonium bromide method (CTAB method).

According to the present invention, detecting existence of a predetermined amplified fragment in the amplification product includes electrophoresis and directly detecting fluorescence signal during the amplification, wherein directly detecting fluorescence signal during the amplification includes detecting signal emitted by labeled specific probe or SYBR® Green and the like by an appropriate fluorescence excitation.

The present invention also provides a kit for identifying transgenic *papaya* line 18-2-4 as described above. In a preferred embodiment of the present invention, the kit further comprises polymerase, deoxyribonucleotide triphosphate and reaction buffer.

The present invention was further illustrated by the following examples; it should be understood that the examples and embodiments described herein are for illustrative purposes only and should not be construed as limiting the embodiments set forth herein.

EXAMPLES

General Materials and Methods
1. Plant Materials

Plants of three different lines of transgenic *papaya* carrying the CP gene of PRSV (Cheng et al., 1996, *Plant Cell Rep*, 16: 127-132) and conferring high degrees of resistance to PRSV (Bau et al., 2003, *Phytopathology*, 93:112-120), including $T_0$ plants of lines 16-0-1, 17-0-5, and 18-2-4; and $T_1$ plants of 16-0-1 and 18-2-4 with hemizygous or homozygous progenies, all micropropagated by tissue culture (Yang et al., 1996, *Plant Cell Rep*, 15:459-464), were used in this study as plant materials. The varieties of non-transgenic *papaya* for comparison were Tainung No. 1, Tainung No. 2 (TN2), Tainung No. 5, Tainung No. 6, Sunrise, Red Lady, Red Ear, Mai Tai Kua, and Thailand. Their seedlings were provided by the National Plant Genetic Resources Center of the Taiwan Agricultural Research Institute (TART) at Wufeng in Taiwan. Plants of the three transgenic lines and all non-transgenic varieties were grown in a contained greenhouse at TARI.

2. *Papaya* Genomic DNA Isolation

*Papaya* genomic DNA was isolated from 0.5 g fresh leaves of the transgenic *papaya* lines and non-transgenic varieties, using cetyltrimethylammonium bromide (CTAB) (SIGMA-ALDRICH Inc., St. Louis, Mo., USA) method (Doyle and Doyle, 1990, *Focus*, 12: 13-15). Poly vinylpolypyrrolidone (PVP, SIGMA-ALDRICH Inc.) was added in the extraction buffer to increase the purity of extracted DNA. DNA concentrations were estimated measuring $OD_{260}$ with a spectrophotometer (U-3000 spectrophotometer, Hitachi Instruments Inc., San Jose, Calif., USA) and DNA quality was analyzed by 1% agarose gel.

3. Transgene-Specific Detection by Polymerase Chain Reaction (PCR)

For category 1 identification, the primer pairs 35S-F/35S-R, npt-1/npt-2, and nos-1/nos-2 (Table 1) were used to detect the *Cauliflower mosaic virus* (CaMV) 35S promoter, the kanamycin selection marker gene npt II, and the nopaline synthase terminator (nos terminator gene), respectively (Holst-Jensen et al., 2003, *Anal Bioanal Chem*, 375: 985-993). For category 2, the primer pair specific for the PRSV CP transgene (Bau et al., 2003, supra), PRSV F/PRSV R, was used (Table 1). For category 3, the primer pairs specific for the promoter and PRSV CP sequence, 35-S/PRSV-R, were used. PCR amplification reaction mixture (final volume 30 μl) contained 128 ng template DNA and 1.2 unit FastStart polymerase (Roche Diagnostics GmbH, Penzberg, Germany), 2.5 mM $MgCl_2$, 200 μM dNTP and 0.2 μM primers in PCR buffer (50 mM KCl, 10 mM Tris-HCl, pH 9.0, 0.1% Triton X-100). The PCR was performed at periods of 1 min at 94° C. for melting, 1 min for annealing (temperature varied for different primer pairs as shown in Table 1), and 2 min at 72° C. for synthesis, for 30 cycles, in a themocycler Gene Amp® PCR System 9700 (Applied Biosystems, Foster City, Calif., USA). The PCR products were analyzed by electrophoresis on 2% agarose gel in TAE buffer (Tris acetate, pH 8.0; 1 mM EDTA).

The PCR products were sequenced directly using 310 Genetic Analyzer (ABI PRISM™, Applied Biosystems). The sequencing procedure of PCR elongation was carried out in a thermocycler for 25 cycles. Following the final elongation, the sequencing products were precipitated, extracted and redissolved in sequencing running buffer (Hi-Di™ Formamide, Applied Biosystems). The samples were then loaded onto the ABI 310 with 61 cm capillary for sequencing. Lasergene software (DNASTAR™, 2001, DNASTAR, Inc., Madison, Wis., USA) was used to align the amplified sequences with specific known sequences.

TABLE 1

The sequence of primers used in the present invention and their corresponding annealing temperatures used in PCR

| Primer/probe | Target | Sequence[a] | $Ta^b$ (° C.) | SEQ ID NO. |
|---|---|---|---|---|
| 35S-F | 35S promoter | [+2475]5'-CAGCTATGACCATGATTACGC-3'[+2495] | 55 | 1 |
| 35S-R | 35S promoter | [+3293]5'-TCTTGCGAAGGATAGTGG-3'[+3310] | 55 | 2 |
| nos-1 | nos terminator | [+1616]5'-TGCCGGTCTTGCGATGAT-3'[+1633] | 55 | 3 |
| nos-2 | nos terminator | [+1720]5'-ATGTATAATTGCGGGACTCTAA-3'[+1741] | 55 | 4 |
| npt-1 | nptII | [+355]5'-ATAATCTGCACCGGATCTGG-3'[+374] | 55 | 5 |
| npt-2 | nptII | [+1164]5'-CCGCTCAGAAGAACTCGTCA-3'[+1183] | 55 | 6 |
| PRSV-F | Transgene | [+3400]5'-TCCAAGAATGAAGCTGTGGA-3'[+3419] | 55 | 7 |
| PRSV-R | Transgene | [+4220]5'-GTGCATGTCTCTGTTGACAT-3'[+4239] | 55° | 8 |
| Ap1 | Adaptor | 5'-GTAATACGACTCACTATAGGGC-3' | 56 | 9 |
| Ap2 | Adaptor | 5'-ACTATAGGGCACGCGTGGT-3' | 56 | 10 |
| S18 | nos promoter | [+213]5'-ACGCGCAATAATGGTTTCTGACG-3'[+235] | 56 | 11 |
| Papa27 | nos promoter | [+96]5'- GCGTCATCGGCGGGGTCATAA-3'[+117] | 55 | 12 |
| P1 | Transgene | [+3704]5'-CAAACACTCGCGCCACTCAA -3'[+3723] | 55 | 13 |
| Papa52 | nos terminator | [+4584]5'-TGTTGCCGGTCTTGCGATGATTAT-3'[+4607] | 55 | 14 |
| Papa34 | nos terminator | [+4817]5'-CAACGTCGTGACTGGGAAAAC-3'[+4837] | 55 | 15 |
| N1 | nos terminator | [+4952]5'-GCCCGCTCCTTTCGCTTTCT-3'[+4971] | 56 | 16 |
| Papa31 | RB flanking | 5'-TTGTTCTAATAAGGTTGCTAC-3' | 55 | 17 |
| Papa32 | RB flanking | 5'-AATATCAAATGGACGTGTTAGTG-3' | 55 | 18 |
| Papa56 | Left border | [+5408]5'-GTTATTAAGTTGTCTAAGCGTCAA-3'[+5431] | 55 | 19 |
| Papa57 | LB flanking | 5'-AGACATATATCATCAAGACCATAGTAG-3' | 55 | 20 |
| Papa58 | Left border | [+4592]5'-GTCTTGCGATGATTATCAT-3'[+4610] | 55 | 21 |
| Papa59 | LB flanking | 5'-TGGTTATCAATATAGCAATTATGTAG-3' | 55 | 22 |
| S9-2 | PRSV CP for qPCR | 5'-AGTAACGCGGCAGAGGCATA-3' | 60 | 23 |

TABLE 1-continued

The sequence of primers used in the present invention and their corresponding annealing temperatures used in PCR

| Primer/ probe | Target | Sequence[a] | Ta[b] (° C.) | SEQ ID NO. |
|---|---|---|---|---|
| S10-2 | PRSV CP for qPCR | 5'-GAGCCCTATCAGGTGTTTTCGA-3' | 60 | 24 |
| S5 | Papain for qPCR | 5'-TGGGTTTGTCATTTGGTGATTTT-3' | 60 | 25 |
| S6 | Papain for qPCR | 5'-GTCTTTCAGTGGATGTCAAGTCATTT-3' | 60 | 26 |
| Fam[c] | PRSV probe | 5'-TTAGTCTCGCTAGATATGCTT-3' | 60 | 27 |
| Vie[d] | Papain probe | 5'-CTATTGTGGGTTATTCTC-3' | 60 | 28 |

[a]Numbers as indicated in individual sequences refer to the position of T-DNA insert.
[b]Ta represents annealing temperature.
[c]The probe was labeled with FAM (excitation: 488 nm; emission: 518 nm) at its 5' end.
[d]The probe was labeled with VIC (excitation: 488 nm; emission: 552 nm) at its 5' end.

4. Preparation of Genomic DNA Fragment and Adaptor Ligation

Uncloned genomic DNA fragments were prepared as described by Sibbert et al. (1995) with required modifications (Sibbert et al., 1995, *Nucleic Acid Res,* 23:1087-1088). The genomic DNAs of the three previously characterized transgenic *papaya* lines, 16-0-1, 17-0-5 and 18-2-4 (Bau et al., 2003, supra), were prepared separately. Different restriction enzymes, DraI (New England Biolabs, Inc., Ipswich, Mass., USA), SspI (Promega, Madison, Wis., USA) and EcoRV (Promega), were separately used to digest individual genomic DNAs (each of 10 µg) for generation of blunt-end fragments. The adaptor containing a long strand and a short complementary strand was prepared by annealing two complementary oligonucleotides: the long strand (48 nts) 5'-GTAATAC-GACTCACTATAGGGCACGCGTGGTC-GACGGCCCGGGC AGGT-3' and the short strand (8 nts), 5'-PO$_4$-ACCTGCCC-NH$_2$-3'. Ligation of the adaptor to the restricted genomic DNA was performed in a final volume of 15 µl containing 1.5 µl 10× Fast-Link™ ligation buffer, 0.75 µl 10 mM ATP, 0.5 µl 100 µM upper and lower strand adaptors, 2 µl restricted genomic DNA libraries and 1 µl Fast-Link DNA ligase (Fast-Link™ DNA Ligation Kits, Epicentre, Madison, Wis., USA). After overnight ligation at 15° C., the solution was placed at 70° C. for 10 min to quench the reaction. High Pure PCR Product Purification Kit (Roche Diagnostics GmbH) was used to purify the reaction products.

5. Nested Polymerase Chain Reaction (Nested PCR)

Figure 1A:
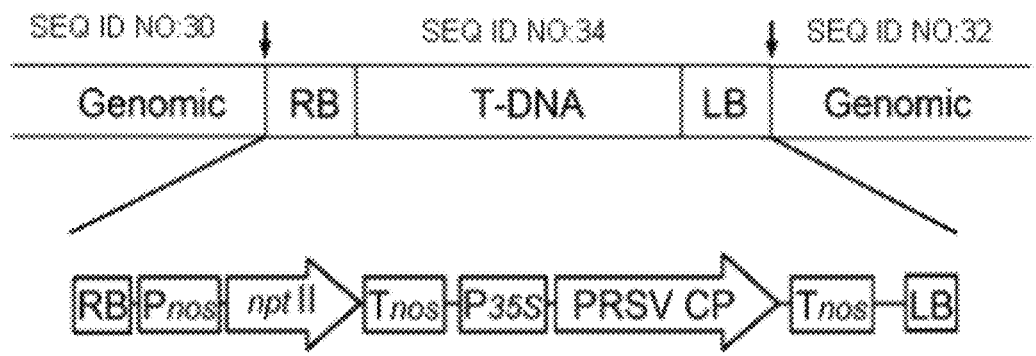
Figure 1B:
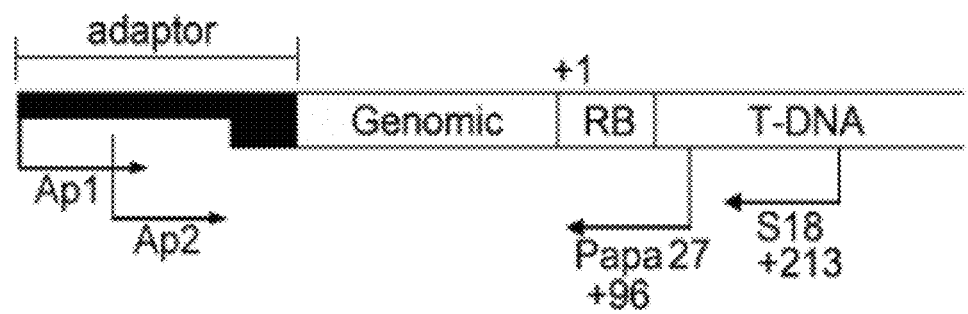
Figure 1C:
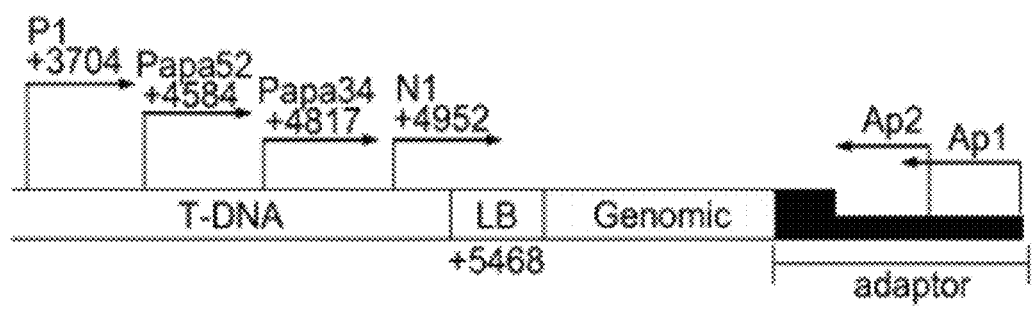

The flanking sequences of the T-DNA insert in *papaya* genome of three transgenic lines were determined by PCR walking from restricted genomic DNA fragments ligated with the adaptor. Since the long strand contained sequences homologous to the two primers, Ap1 and Ap2 (Table 1) (Zheng et al., 2001, *Transgenic Res,* 10: 237-245; Zheng et al., 2001, *Mol Breeding,* 7:101-115), they were used to anneal to the adaptor. The T-DNA-specific primers were designed to match sequences near the right border (RB) or the left border (LB) region (FIGS. 1*a*, *b*, and *c*). For the three transgenic lines, the primers S18 and Papa27 near the RB region were designed to match regions in the contexts +235 to +213 and +117 to +96 from the first nucleotide of the RB, respectively (Table 1, FIG. 1*b*). For the transgenic line 18-2-4, the primers near the LB region, P1 and Papa52, were designed to match regions in the contexts +3704 to +3723 and +4584 to +4607 from the first nucleotide of RB, respectively (Table 1, FIG. 1*c*). For the transgenic lines 16-0-1 and 17-0-5, the primers near LB region, Papa34 and N1, were designed to match regions in the contexts +4817 to +4837 and +4952 to +4971 from the first nucleotide of RB, respectively (Table 1, FIG. 1*c*).

For the RB region, primary PCR was conducted in a 30 µl reaction mixture containing 128 ng restricted DNA fragments ligated with the adaptor, 1.2 unit FastStart polymerase (Roche Diagnostics GmbH), 2.5 mM MgCl$_2$, 200 µM dNTP and 0.2 µM primers S18 and Ap1 in PCR buffer (50 mM KCl, 10 mM Tris-HCl, pH 9.0, 0.1% Triton X-100). PCR was conducted after a hot start at 94° C. for 1 min, followed by a fixed denaturing step at 94° C. for 30 sec. The first six cycles were conducted with an initial annealing temperature of 61° C. for 30 sec, followed by a decline at the rate of 1° C. every cycle. The extension step was performed at 72° C. for 3 min in each cycle. Additional 30 cycles were conducted with denaturing at 94° C. for 30 sec, annealing at 56° C. for 30 sec and extension at 72° C. for 3 min with an increase in time at the rate of 10 sec every cycle. PCR was terminated after a final extension for 5 min at 72° C. Secondary PCR were conducted with 1000-fold dilution of primary PCR using nested adaptor primer Ap2 and the nested RB-specific primer Papa27 (Table 1). The components of PCR reagent mixture were the same as those for the primary PCR.

A similar amplification was also performed with the primer pair specific to the LB region. Primers Papa34 and Ap1 were used for amplifying the LB region of 16-0-1 and 17-0-5 lines. Primers P1 and Ap1 were used for amplifying the LB region of 18-2-4 line (Table 1 and FIG. 1*a* to *c*). For the secondary PCR, the primers N1 and Ap2 were used for lines 16-0-1 and 17-0-5, and Papa52 and Ap2 for line 18-2-4. The products of secondary PCR were analyzed by electrophoresis on 2% agarose gel.

6. Determination of Genomic Sequences Flanking the Transgene

Secondary amplified products from nested PCR were cloned in TOPO TA vector according to manufacturer's instructions (Invitrogen, Carlsbad, Calif., USA) and selected plasmid DNA was isolated using Spin Miniprep Kit (Qiagen GmbH, Hilden, Germany) Purified plasmids were used for sequencing by 310 Genetic Analyzer (Applied Biosystems).

The genomic flanking sequences and the T-DNA border sequences were assembled and analyzed by Lasergene software (DNASTAR, Inc.) and CpGDB (A *Carica papaya* Plant Genome Database, http://www.plantgdb.org/CpGDB/) (Ming et al., 2008, *Nature*, 452: 991-996).

7. Event-Specific Identification of Transgenic *Papaya* Lines

For the category 4 event-specific detection, specific primers matched the T-DNA sequences near the RB or LB border, including Papa27, 57, and 59 that were used for nested PCR (Table 1), were coupled with specific primers designed from the elucidated genomic flanking sequences to amplify the regions across each T-DNA border. Primers Papa31 and Papa56 (Table 1) were designed from the sequences flanking the RB and LB borders of line 16-0-1, respectively. Primers Papa32 and Papa58 (Table 1) were designed to match the sequences flanking the RB and LB borders of line 18-2-4, respectively. PCR was conducted in a 30 µl reaction mixture containing 1.2 unit FastStart polymerase (Roche Diagnostics GmbH), 2.5 mM MgCl$_2$, 200 µM dNTP, 0.2 µM of appropriate primer pair as described above, and 128 ng genomic DNA of 16-0-1, 17-0-5 or 18-2-4 in PCR buffer (50 mM KCl, 10 mM Tris-HCl, pH 9.0, 0.1% Triton X-100). The reaction was started with an initial denaturing step at 94° C. for 2 min, followed by denaturing at 94° C. for 1 min, annealing at 61° C. for 1 min and extension at 72° C. for 2 min. After a total of 30 cycles, the reaction was terminated by a 5 min extension step at 72° C. PCR products were analyzed by electrophoresis on 2% agarose gel.

8. Analysis of the Endogenous Sequence Inserted with T-DNA

The primer pairs Papa31/Papa57 (for both lines of 16-0-1 and 17-0-5) and Papa32/Papa59 (for line 18-2-4) designed to match the flanking genomic sequences of T-DNA of transgenic lines were applied to analyze the endogenous sequence of non-transgenic *papaya*, where T-DNA is inserted. Sample DNAs of 16-0-1, 17-0-5, 18-2-4, TN2, 16-0-1 homozygote and 18-2-4 homozygote were used for analysis. PCR was conducted in a 30 µl reaction mixture containing 0.75 unit FastStart polymerase (Roche Diagnostics GmbH), 200 µM dNTP, 0.2 µM primers, and 128 ng genomic DNA of each sample, in PCR buffer (50 mM Tris/HCl, 10 mM KCl, 5 mM (NH$_4$)$_2$SO$_4$, 2 mM MgCl$_2$, pH 8.3/25° C.). The reaction was started with an initial denaturing step at 94° C. for 2 min, followed by 30 cycles of denaturing at 94° C. for 1 min, annealing at 55° C. for 1 min and extension at 72° C. for 2 min. The reaction was terminated after a 10 min final extension at 72° C. The PCR products were examined on 2% agarose gel, cloned and sequenced as described above. DNA sequence analyses were carried out using the BLAST program and the ORF Finder (http://www.ncbi.nlm.nih.gov/).

9. Southern Blotting

Sample DNAs of 16-0-1, 18-2-4, TN2, 16-0-1 homozygote, 18-2-4 homozygote, and 16-0-1 outcrossed with an unidentified PRSV CP transgenic line were used for analysis. Fifty micrograms of genomic DNA isolated from transgenic and non-transgenic *papaya* were digested with 5 unit EcoRI (Promega) at 37° C., overnight. After separation on a 0.8% agarose gel, the DNA was transferred to nylon membrane (AMERESCO Inc., Solon, Ohio, USA). A digoxigenin-labeled probe corresponding to the PRSV CP gene was prepared by PCR using DIG Luminescent Detection Kit (Roche Diagnostics GmbH). After hybridization overnight at 60° C., the membranes were stringently washed at 65° C. in washing buffer (0.5×SSC, 0.1% SDS). The probe-positive bands were visualized by exposing the light emission of dephosphorylated chemiluminescence substrate CSPD (Disodium 3-(4-methoxyspiro{1,2-dioxetane-3,2'-(5'-chloro)tricyclo [3.3.1.13,7]decan}-4-yl)phenyl phosphate, Roche Diagnostics GmbH) to X-ray film (BioMax Light Film, Kodak, Paris, France).

10. Detection of the Copy Number of Inserted T-DNA by Real Time PCR

The copy numbers of the inserted transgene in the T$_0$ lines 16-0-1 and 18-2-4 and their corresponding homozygote progenies were further analyzed by relative quantitative real-time PCR of the transgene (PRSV CP gene) by ABI PRISM® 7000 Sequence Detection systems (Applied Biosystems), using the endogenous papain gene as a control. Transgene-specific primer pair S9-2/S10-2 and papain gene-specific primer pair S5/S6; and TaqMan fluorescent dye-labeled transgene-specific probes for real-time PCR, Fam (transgene-specific) and Vic (papain-specific), are listed in Table 1. The following reagents were used for amplification in 25 µl: 5 µl DNA (50 ng for each sample.), 0.6 µM of each primer, 12.5 µL 2× Master Mix (Applied Biosystems) and 250 nM papain or PRSV probe. The final volume was adjusted with sterile water. The thermal cycling conditions were initially 2 min at 50° C. and 10 min at 95° C., followed by 40 cycles at 95° C. for 15 seconds and 60° C. for 1 min The PCR was performed in a 96-well clear optical reaction plate. Each sample was assayed in triplicate, and analyzed with the SDS software 1.1 (Applied Biosystems) and Microsoft Excel.

During the log-linear phase, amplification was described by $N=No(1+E)^n$, where N is the number of amplified molecules, No is the initial number of molecules, E is the amplification efficiency, and n is the number of cycles. If the amplification efficiency was similar for the two reactions, the initial concentration of the sample was calculated on the basis of the above formula by the comparative delta Ct method (Livak and Schmittgen, 2001) and the gene copy number was given by the formula $2^{-(\Delta\Delta Ct)}$, where $\Delta\Delta Ct=(Ct_{PRSV}$ sample$-Ct_{papain}$ sample$)-(Ct\ PRSV_{calibrator}-Ct\ papain_{calibrator})$, which was defined as the point at which the fluorescence level rises above the baseline.

Example 1

Category 1, 2, and 3 Detection for Transgenic *Papaya* Lines

In the present example, Category 1, 2, and 3 detection was carried out by methods as described in "General materials and methods".

For category 1 detection, the inserted CaMV 35S promoter (FIG. 2, panel a), npt II (FIG. 2, panel b), and nos terminator were targeted to determine the presence of a possible T-DNA integration. The primer pairs 35S-F/35S-R designed to CaMV 35S promoter amplified an 836 bp product (FIG. 2, panel a) from the three transgenic lines. This DNA amplicon was not found in all untransformed lines. Similarly, the primer pair npt-1/npt-2 for npt II amplified a specific 829 bp product (FIG. 2, panel b) from the three transgenic lines. The nos promoter-specific primer pair nos-linos-2 amplified a specific 126 bp product (FIG. 2, panel c) from the three transgenic lines.

Figure 2:
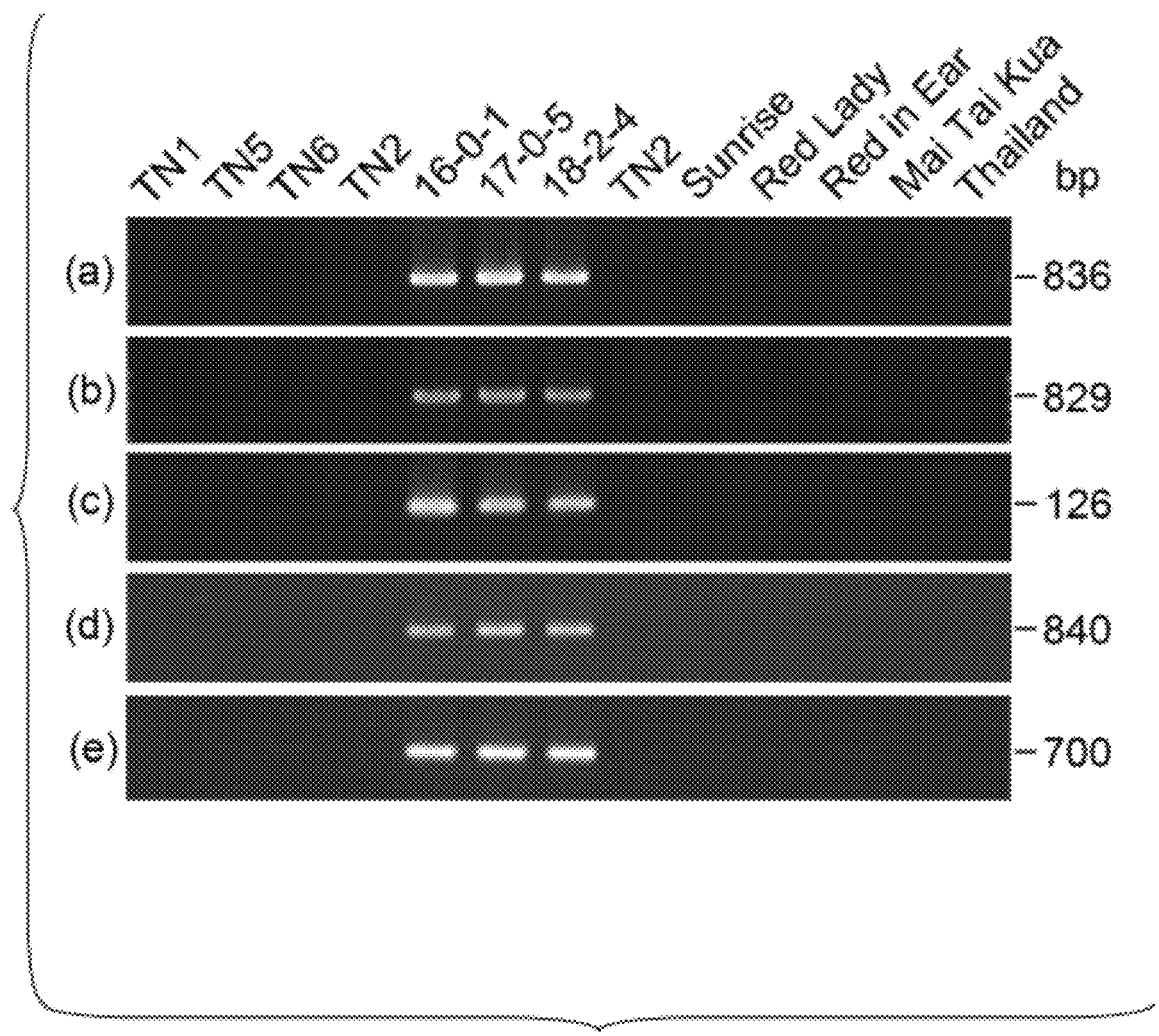
FIG. 2 illustrates results of PCR detection of category 1, 2, and 3 to identify transgenic *papaya* lines from non-transgenic varieties, wherein panel (a) illustrates results of category 1 detection for 35S promoter using 35S promoter-specific primer pair 35S-F/35S-R that amplified a product of 836 bp; panel (b) illustrates results of category 1 detection for the neomycinphospotransferase II selection marker gene (npt II) using npt II-specific primer pair npt-1/npt-2 that amplified a product of 829 bp; panel (c) illustrates results of category 1 detection for the nopaline synthase terminator (nos terminator) using nos terminator-specific primer pair nos-1/nos-2 that amplified a product of 126 bp; panel (d) illustrates results of category 2 detection for the transgene using PRSV coat protein gene-specific primer pair PRSV-F/PRSV-R that amplified a product of 840 bp; and panel (e) illustrates category 3 detection for the region between CaMV 35 S promoter and PRSV CP transgene using the primer pair 35S-F/PRSV-R that amplified a product of 700 bp.

For category 2, the primer pair PRSV-F/PRSV-R designed from the CP gene of PRSV generated a product of 840 bp specific to the three transgenic lines (FIG. 2, panel d).

For category 3 detection, with the primer pair designed for specific detection of the region across the CaMV 35S promoter and PRSV CP coding sequence, a product of 700 bp was specifically amplified from the three transgenic lines (FIG. 2, panel e).

All specific products from the category 1, 2, and 3 detections were sequenced to verify their sequence fidelity to the targeted regions. In order to analyze the sensitivity of the detection, the applicants combined the DNA extracts from untransformed and transgenic *papaya* in different ratios. The results indicated that the specific fragments could be detected, when the presence of each transgenic line was at 1% level (a ratio of 99/1, non-transformed/transgenic).

Example 2

Amplification of the Regions Covering Flanking Sequences of T-DNA and Elucidation of T-DNA Flanking Sequences In the present example, the regions covering flanking sequences of T-DNA was amplified and the amplified product was further cloned and analyzed flanking sequences of T-DNA therein by methods as described in "General materials and methods".

The genomic sequences that flank the T-DNA insert of the transgenic *papaya* lines were amplified by AL-PCR. In nested PCR, with primers Papa27 (SEQ ID NO:12) and Ap2 (SEQ ID NO: 10), specific to T-DNA and the ligated adaptor, respectively, a product of 464 bp was amplified from a SspI-digested DNA of lines 16-0-1 or 17-0-5, whereas a 543 bp product was obtained from line 18-2-4. In nested PCR of lines 16-0-1 and 17-0-5, with primers N1 (SEQ ID NO: 16) and Ap2 (SEQ ID NO: 10) specific to T-DNA and the adaptor, respectively, a major product of 771 bp was amplified from a DraI-digested DNA of lines 16-0-1 or 17-0-5. A product of 724 bp was obtained from line 18-2-4, using an EcoRV-digested DNA and primers Papa52 (SEQ ID NO: 14) and Ap2 (SEQ ID NO: 10).

The amplified products of the nested PCR from all the transgenic lines were cloned and sequenced. All the analyzed DNAs contained the sequence of the T-DNA specific primer at one end and the adaptor primer at the other end. This suggests that the nested PCR products covered the genomic sequences that flank the T-DNA insert.

Figure 3A:
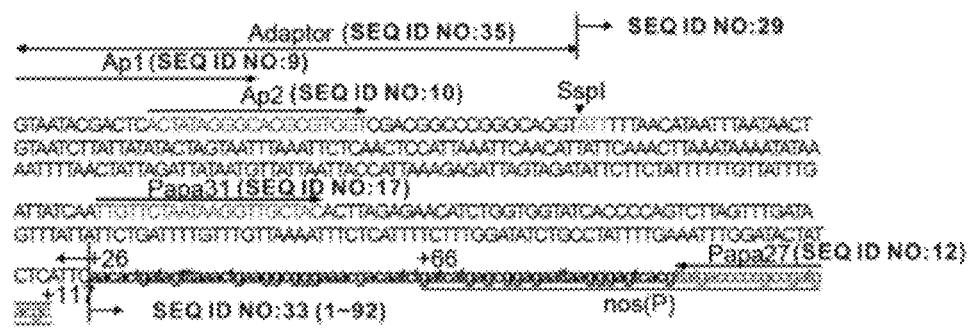
FIGS. 3*a* and 3*b* illustrate the results of sequence analysis of T-DNA right border/*papaya* genomic DNA junctions, wherein the T-DNA sequence and its right border are shown in lower case; *papaya* genomic DNA sequences that flank the right border are shown in upper case; the recognition sites (ATT) of SspI in genomic DNA are indicated by an arrow head; the positions of the primers Ap1 (SEQ ID NO: 9), Ap2 (SEQ ID NO: 10), Papa27 (SEQ ID NO: 12), Papa31 (SEQ ID NO: 17), and Papa32 (SEQ ID NO: 18) that are used for amplification are also indicated.
Figure 3B:
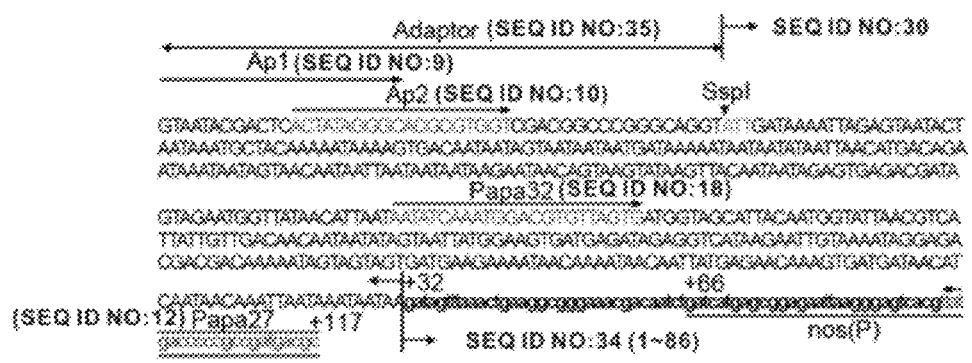

For the sequence that flank the RB of T-DNA, the amplified DNAs of lines 16-0-1 and 17-0-5 were consisted of a 92 bp of T-DNA sequence (+26~+117) and lacked the RB sequence (+1~+25). However the amplified DNAs possessed a partial sequence of nopaline synthase promoter (FIG. 3a), a 337 bp *papaya* genomic sequence with a SspI cleavage site (AAT) (SEQ ID NO: 29) and a 48 bp adaptor sequence (SEQ ID NO:35) (FIG. 3a). The product amplified from the RB region of the transgenic line 18-2-4 DNA contained a genomic sequence of 422 bp that is extended with a SspI recognition site AAT (SEQ ID NO: 30), a 48 bp adaptor sequence (SEQ ID NO:35) and the partial nopaline synthase promoter sequence (+31~+117) of 86 bp without the complete RB sequence (+1~+30) (FIG. 3b).

Figure 4A:
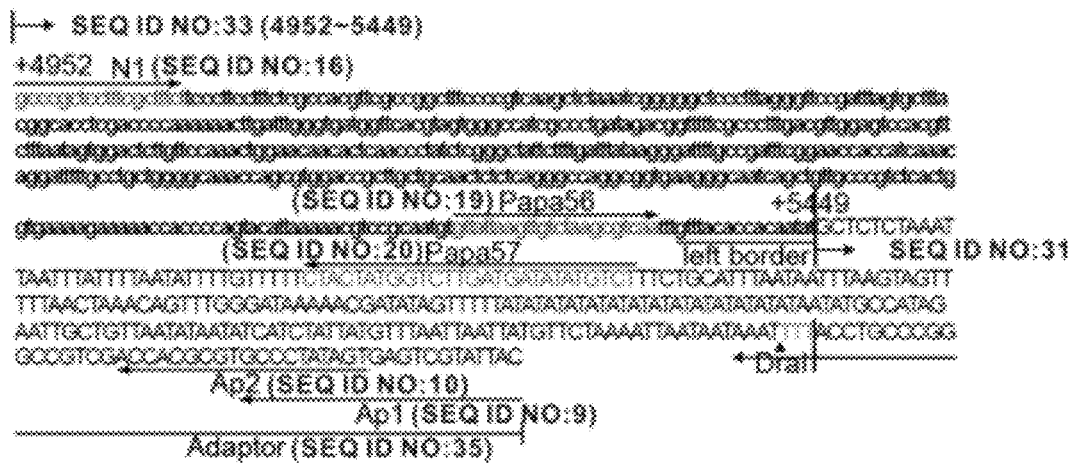
FIGS. 4*a* to 4*b* illustrate the results of sequence analysis of T-DNA left border/*papaya* genomic DNA junctions, wherein the T-DNA sequences near its the left border are shown in lower case; *papaya* genomic sequences that flanking the T-DNA right border are shown in upper case; the restriction enzymes DraI and EcoRV recognition sites, TTT and GAT, respectively, in genomic DNA are indicated; and the positions of the specific primers Apt (SEQ ID NO: 9), Ap2 (SEQ ID NO: 10), Papa52 (SEQ ID NO: 14), Papa56 (SEQ ID NO: 19), Papa57 (SEQ ID NO: 20), Papa58 (SEQ ID NO: 21), Papa59 (SEQ ID NO: 22), and N1 (SEQ ID NO: 16) that are designed for amplification are also presented.
Figure 4B:
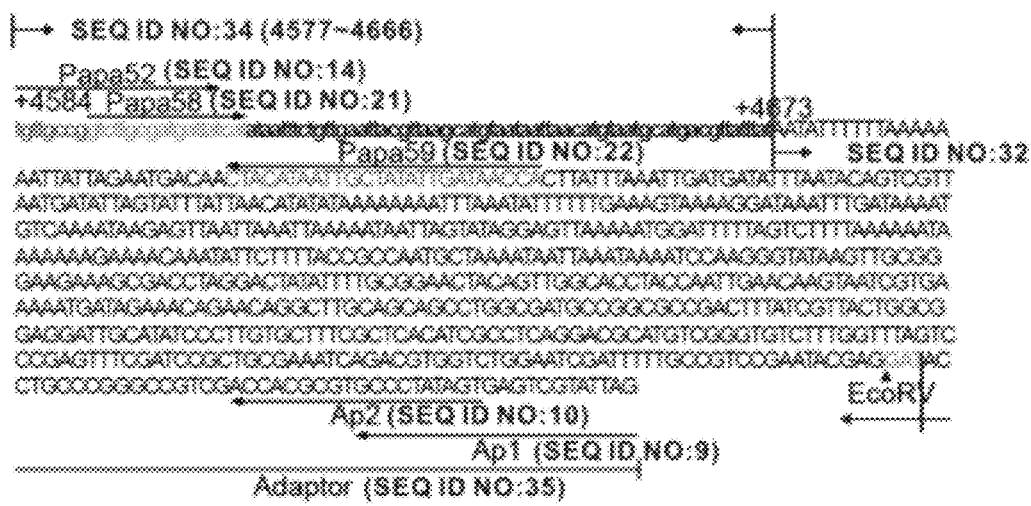

For the sequence that flank the LB of T-DNA, the amplified products of lines 16-0-1 and 17-0-5 were consisted of a 498 bp T-DNA sequence (+4952~+5449) with an incomplete T-DNA left border sequence (16 bp), a 237 bp genomic sequence with a DraI recognition site (TTT) (SEQ ID NO: 31) and a 48 bp adaptor sequence (SEQ ID NO:35) (FIG. 4a). The amplified product of 18-2-4 contained a 90 bp T-DNA sequence (+4584~+4673) that was devoid of LB sequence, and a 599 bp genomic sequence with an EcoRV recognition site (GAT) (SEQ ID NO: 32) and a 48 bp adaptor sequence (SEQ ID NO:35) (FIG. 4b).

Example 3

Detection of Transgenic *Papaya* Lines by Flanking-Sequence Specific Primers

The primers Papa31 (FIG. 3a) and Papa32 (FIG. 3b), which were designed from T-DNA RB flanking sequences from lines 16-0-1 and 18-2-4, respectively, were used for identifying the corresponding transgenic *papaya* lines by methods as described in "General materials and methods". From the transgenic lines 16-0-1 and 17-0-5, a specific product of 241 bp (FIG. 5, panel a) was obtained with the primer pair Papa31/Papa27, but no product was found from line 18-2-4. For line 18-2-4, a specific product of 384 bp (FIG. 5, panel b) was obtained with the primer pair Papa32/Papa27, but no other products were amplified from lines of 16-0-1 and 17-0-5 (FIG. 5, panel b).

For the LB flanking sequence, the primer pairs Papa56/Papa57 (FIG. 4a) and Papa58/Papa59 (FIG. 4b) were designed for identifying the three transgenic *papaya* lines. The primer pair Papa56/Papa57 amplified a specific product of 106 bp (FIG. 5, panel c) from lines 16-0-1 and 17-0-5, but not from line 18-2-4. Whereas, the primer pair, Papa58/Papa59 amplified a specific product of 140 bp (FIG. 5, panel d) from line 18-2-4, but not from lines 16-0-1 and 17-0-5.

Figure 5:
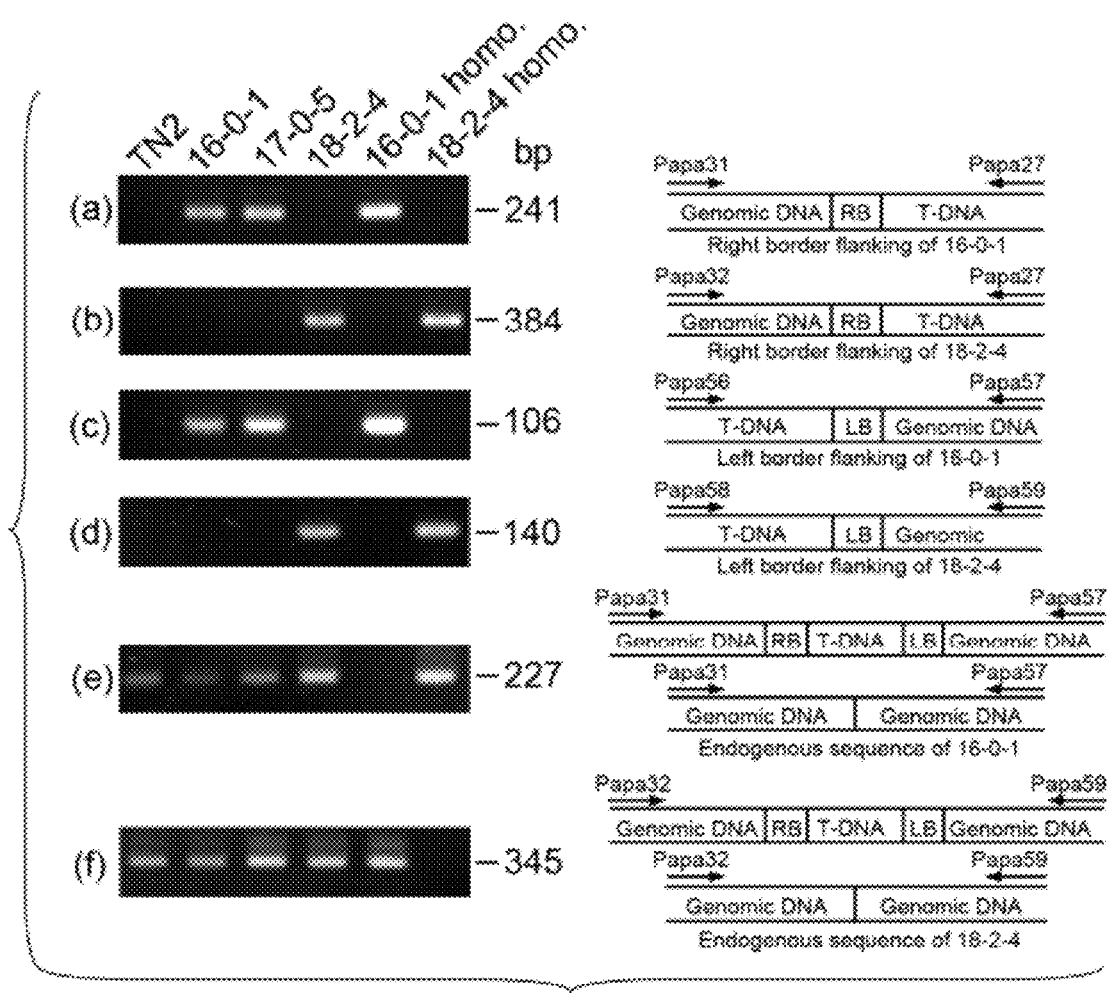
FIG. 5 illustrates results of event-specific detection of transgenic *papaya* lines using the primers specific to genomic flanking sequence and T-DNA sequence to generate a DNA product across T-DNA right border and plant genome, or a product across T-DNA left border and plant genome by PCR, wherein the positions and combination of primers are indicated.

When the primer pair Papa31/Papa57 was used for PCR detection, a fragment of 227 bp with identical sequence was amplified from lines 16-0-1, 17-0-5, 18-2-4, 18-2-4 homozygous progeny, and untransformed TN2, while this product was not detected from the 16-0-1 homozygous progeny (FIG. 5, panel e). When the primer pair Papa32/Papa59 was used for PCR detection, a fragment of 345 bp with identical sequence, was amplified from lines 16-0-1, 17-0-5, 18-2-4, 16-0-1 homozygous progeny, and untransformed TN2, which was not detected from the homozygous progeny of 18-2-4 (FIG. 5, panel f). The two PCR products were sequenced and analyzed with NCBI database, but no significant homology was found. The PCR product amplified by the primer pair Papa31/Papa57 did not contain any open reading frame to be shown by the ORF Finder. The PCR product amplified by the primer pair Papa32/Papa59 was found to possess a 48 amino acid reading frame, the BLASTP analysis of which did not show any similar sequence from protein databases.

Example 4

Determining Transgenic *Papaya* Line by Southern Blotting

Since the restriction enzyme EcoRI used for Southern analysis cleaves only once within the T-DNA, the single signals of 10 kb and 4 kb resulted from $T_0$ lines 16-0-1 and 18-2-4, respectively (FIG. 6), indicated that there is only one copy T-DNA insert in these lines. The blot signals of transgenic *papaya* homozygous progenies of both 16-0-1 and 18-2-4 were at the same position as hemizygous $T_0$ lines, but the intensity was much stronger. As shown in FIG. 6, it was found that two insertion sites in the progeny from the 16-0-1 crossed with an unidentified transgenic line carrying the same PRSV CP construct, one fragment with molecular size similar to that from line 16-0-1 and the other was 6 kb that was apparently derived from the other transgenic *papaya* line.

Example 5

Copy Numbers Determined by Real-Time PCR

In the present example, by comparing the copy numbers of the T-DNA inserts in the transgenic *papaya* lines 18-2-4, 16-0-1 homozygous progeny, and 18-2-4 homozygous progeny using line 16-0-1 as the calibrator, zygosity of the transgenic *papaya* was analyzed by real-time PCR by methods as described in "General materials and methods". The fold change was predicted to be 1 for hemizygous $T_0$ plants and 2 for homozygous $T_1$ plants. The amplification plots are shown in FIG. 7 Amplification plots for the 16-0-1 homozygous $T_1$ plant (b) and 18-2-4 homozygous $T_1$ plant (d) were similar to that of the papain gene control. A shift to the left, when compared to the PRSV CP amplification plot for the 16-0-1 hemizygous $T_0$ plant (a) and 18-2-4 hemizygous $T_0$ plant (c) was noticed, indicating an increased copy number of transgene in both cases. Real-time PCR-derived copy number values for T-DNA insert are summarized in Table 2. Using line 16-0-1 as the calibrator, the relative copy number for transgenic line 18-2-4 was estimated as 0.85, for 16-0-1 homozygous progeny, as 2.04 and for 18-2-4 homozygous progeny 2.12.

TABLE 2

Copy number analysis for transgenic papaya lines

| Transgenic papaya lines | $\Delta Ct$ ($Ct_{PRSV}$ − $Ct_{papain}$) ± SD$^a$ | Copy number in 16-0-1 as calibrator ($2^{-\Delta\Delta Ct}$) |
|---|---|---|
| 16-0-1 | 2.13 ± 0.03 | 1.00 |
| 18-2-4 | 2.37 ± 0.09 | 0.85 |
| 16-0-1 homozygous | 1.11 ± 0.04 | 2.04 |
| 18-2-4 homozygous | 1.05 ± 0.06 | 2.12 |

$^a$average of three measurements

In the previous examples, the applicants used PCR-based techniques for identifying indicated transgenic *papaya* lines that provide broad-spectrum resistance to different PRSV strains from various geographic origins, including category 1 for screening, category 2 for gene-specific detection, category 3 for construct-specific detection and category 4 for event-specific detection, according to their levels of specificity. Because the results of all four levels of PCR detection for lines 16-0-1 and 17-0-5 were identical, the applicants conclude that these two lines actually originated from a common line. On the other hand, lines 16-0-1 and 18-2-4 were independent transgenic lines derived from two unique transformation events, although they are from the same variety transformed by the same T-DNA construct and confer similar degrees of broad-spectrum resistance to different PRSV strains (Bau et al. 2003, supra; Bau et al., 2004, *Plant Dis*, 88: 594-599).

A plant vector for transformation normally consists of several elements, including at least a gene of interest, a promoter functioning as a transcription start signal, a terminator functioning as a termination signal for regulation of gene expression, and a selection marker. Since most of the transgenes introduced into plant genome contain CaMV 35S promoter, nos terminator and npt II selection marker gene, these components are detected using specific primer pairs in primary screening of transgenic plants. Nevertheless, there are more and more types of promoters and selection markers being used in plant transformation. In the present invention, specific primers for detecting the presence of the CaMV 35S promoter, the nos terminator, and the npt II marker (Holst-Jensen et al., 2003, supra) were used for identifying transgenic *papaya* lines. The results in accordance with the previous examples indicate that specific PCR products amplified with these primers are reliable markers for identifying a possible transgenic *papaya* plant. However, this primary screening method can not be solely used to identify a specific GM crop, since the presence of one of the screening targets does not necessarily imply the presence of a foreign DNA insert, because the source of a 35S promoter from CaMV or a nos terminator from Ti-plasmid is naturally occurring (Wolf et al., 2000, *Eur Food Res Technol*, 210: 367-372). Moreover, it is generally believed that soil bacteria containing one or more of the npt II selection marker, which is a naturally occurring transposon, are present in soil (Lo et al., 2007, *J Agri Food Chem*, 55: 7534-7540).

For category 2 detection, the gene of interest may also be of natural origin, but is often slightly modified, including, by truncation or codon usage alternation (Hemmer, 1997, BATS-report 2/97: Foods derived from genetically modified organisms and detection methods. BATS, Basel, Switzerland). Furthermore, choice for available gene is more specific than the choice for available promoters and terminators. Consequently, PCR methods targeting the gene of interest are more specific than category 1 detection. The results of category 2 are normally used to prove that a particular transgenic line contains a specific transgene which is consequently utilized by breeders for a particular function.

For category 3, the positive signal only appears in the presence of GM-derived material and can be used to identify the GM source of the DNA more specifically than the category 2. In the present invention, PRSV CP gene-based primers in accordance with the present invention amplified a unique PCR product (840 bp) from all the three transgenic *papaya* lines carrying the same PRSV CP transgene. Also, the region-based (35S promoter+PRSV CP) primers amplified another unique PCR product (700 bp) only from the three transgenic *papaya* lines. The applicants believe that these category 2 and 3 molecular markers can be used for identifying any transgenic lines derived from the PRSV CP construct used for *papaya* transformation. Also, these markers are reliable tools for identifying the presence of the transgene in a particular progeny during the process of molecular breeding.

Category 4 aims at detecting the junction at the integration locus between the *papaya* genome and the inserted DNA. This is the most unique feature of a transformation event (Zheng et al., 2001, supra; Holst-Jensen et al., 2003, supra). Together with the sequencing data, the AL-PCR results provided evidence for the true integration of the T-DNA construct into the *papaya* genome. Secondly, it can determine the T-DNA insert number and their integrity. It was also possible to determine and analyze nucleotide sequence of the genomic locus at which the T-DNA was integrated. Different restriction enzymes for blunt-end cleavage were chosen, because they yielded different pools of fragments, to which blunt-end adaptors could be easily ligated (Zheng et al., 2001, supra). The restriction-enzyme digested fragments which were too long for PCR amplification would escape detection. Therefore, the use of several preparations generated by different restriction enzymes would reduce the risk of missing inserted sequences. Furthermore, T-DNA-specific primers were designed as close as possible to the border sequences to generate appropriate flanking sequences. On the other hand, adaptor was designed to have one staggered end complementary to that of the restricted genomic DNA. This allows specific ligation of the adaptor with restricted genomic DNA, but not with fragments of broken DNA present in some DNA preparation. The short adaptor strand was not phosphorylated to prevent its ligation to any restriction fragment and to consequently ensure that it would be lost from the adaptor during the first heating step of PCR.

The event-specific PCR methods using the primer pairs designed from the flanking sequences and the T-DNA sequence to analyze the transgenic *papaya* lines can be used as the molecular characteristics for intellectual protection of individual transgenic lines. Since all progenies derived from the transgenic lines 16-0-1 and 18-2-4 contain the specific T-DNA inserts with the same flanking sequences, the category 4 detection protocol can also be used to generate molecular markers for identification of the pollen donor from a specific transgenic *papaya* line for pollen flow experiments or for identification of zygosity of the transgene in individual progenies during breeding process. Also, these molecular marker derived from specific flanking sequences can be used for monitoring a specific GMO during production or in markets. USA and Canada use product-related approach and voluntary labeling for their commercialized GM crops, whereas EU countries takes more precaution using process-related approach and mandatory labeling (Carter and Gruere, 2006, Regulating Agricultural Biotechnology: Economics and Policy, Springer, US, pp 459-480). Therefore, these even-specific markers have become a requirement in EU countries and some East Asia countries, such as Taiwan and Japan.

If a transgene is present in a hemizygous condition, like the case of $T_0$ plants, the amplification of the genomic sequences of transgenic *papaya* by the primers designed to the two flanking sequences should amplify two different fragments, a larger product containing the whole T-DNA with parts of the two flanking sequences and a smaller product containing only the endogenous sequence. Transgenic *papaya* lines used in previous examples carry a 5.4 kb T-DNA construct (Cheng et al., 1996, supra) in between the two flanking sequences. Apparently, the fragment containing the whole T-DNA was too large to be amplified by FastStart® Taq polymerase used in the present invention. But, the corresponding locus without T-DNA insertion would still generate an amplified product similar to that of non-transgenic *papaya*. In a homozygous progeny, the large amplified products can not be amplified, since the T-DNA is inserted at the same locus of the diploid chromosome and thus there is no small fragment from the non-inserted endogenous sequences. The event-specific primers designed from the flanking sequences of lines 16-0-1 (Papa31/Papa57) and 18-2-4 (Papa32/Papa59) amplified the specific products of 227 bp and 345 bp from the $T_0$ hemizygous plants, but not from the homozygous progenies (FIG. 5). The presence of the transgene in the tested plants is assured by the positive reactions of category 1-3 detection. Thus, these event-specific primers are suitable for prompt identification of a homozygous progeny derived from lines 16-01 or 18-24 in breeding program. Also, in addition to the inserted transgene, these markers can be used for intellectual protection for any PRSV-resistant varieties derived from lines 16-01 and 18-2-4. Since breeding of a fruit tree, like *papaya*, takes a long time, application of these molecular markers can greatly shorten the breeding program of fixing the PRSV CP transgene in a homozygous parental line for generating a specific hybrid variety resistant to PRSV.

The most commonly used method of determining copy numbers is Southern blotting, in which a blot of digested genomic plant DNA is hybridized with a DNA probe corresponding to the transgene to produce an informative hybridization pattern. The applicants could determine two T-DNA insertion sites in unknown transgenic *papaya* according to Southern analysis, but the number of homozygous line bands does not correspond to the copy number (FIG. 6). In practical detection, the homozygote should have two-fold stronger signals as compared to that of the hemizygous control. Since the hybridization signals of homozygous progenies were much stronger than those of hemizygous individuals from the homozygous *papaya* progenies (FIG. 6), the results of Southern analysis can also be used as an important reference for zygosity determination.

Distinguishing second-generation homozygous lines ($T_1$) from hemizygous transgenic plants ($T_0$) is a key step in developing plant lines which are genetically stable and yield the optimal level of transgene expression. Traditionally, $T_1$ plants are screened for zygosity by a time-consuming segregation analysis of their $T_2$ progeny, which necessitates growing the $T_1$ plant lines to maturity for the collection of their seeds to be germinated on selection media for screening. Using quantitative real-time PCR allows relative quantification of gene copy number, and hence can be used to determine zygosity (Bubner and Baldwin, 2004, *Plant Cell Rep*, 23: 263-271; Ji et al., 2005, *Anal Biochem*, 344-240-246; Prior et al., 2006, *Transgenic Res*, 15:261-265; shitara et al., 2004, *Transgenic Res*, 13: 191-194; Tesson et al., 2002, *Transgenic Res*, 11: 43-48). In the present invention, the homozygous and hemizygous transgenic *papaya* lines were distinguishable by real-time PCR method for determining zygosity. Therefore, the real-time PCR using the primers specific to the transgene coupled with PCR detection with the event-specific primers designed from the flanking sequences are considered a fast and reliable method to identify the zygosity of transgenic plants. Both are useful as a fast screening tool during the breeding process, especially for long-term fruit crops, including *papaya*.

Even though numerous characteristics and advantages of the present invention have been set forth in the foregoing description, together with details of the structure and features of the invention, the disclosure is illustrative only. Changes may be made in the details within the principles of the invention to the full extent indicated by the broad general meaning of the terms in which the appended claims are expressed.

What is claimed is:

1. A primer pair for amplifying a transgenic *papaya* nucleic acid sequence, which consists essentially of a nucleic acid fragment having the sequence set forth in SEQ ID NO: 18; and a nucleic acid fragment having the sequence set forth in SEQ ID NO: 22.

* * * * *